(12) United States Patent
Heyden et al.

(10) Patent No.: US 11,534,740 B2
(45) Date of Patent: Dec. 27, 2022

(54) OXIDATION BY USE OF ELECTRONIC ATOMIC MONOLAYER-METAL SUPPORT INTERACTION CATALYSTS

(71) Applicant: UNIVERSITY OF SOUTH CAROLINA, Columbia, SC (US)

(72) Inventors: Andreas Heyden, Columbia, SC (US); Yongjie Xi, Columbia, SC (US)

(73) Assignee: University of South Carolina, Columbia, SC (US)

( * ) Notice: Subject to any disclaimer, the term of this patent is extended or adjusted under 35 U.S.C. 154(b) by 170 days.

(21) Appl. No.: 16/821,337

(22) Filed: Mar. 17, 2020

(65) Prior Publication Data

US 2020/0360902 A1   Nov. 19, 2020

Related U.S. Application Data

(60) Provisional application No. 62/849,277, filed on May 17, 2019.

(51) Int. Cl.
| | | |
|---|---|---|
| *B01J 23/755* | (2006.01) | |
| *B01J 35/02* | (2006.01) | |
| *B01J 35/00* | (2006.01) | |
| *B01J 37/02* | (2006.01) | |
| *C07C 29/48* | (2006.01) | |
| *C07C 31/04* | (2006.01) | |

(52) U.S. Cl.
CPC ......... *B01J 23/755* (2013.01); *B01J 35/0006* (2013.01); *B01J 35/02* (2013.01); *B01J 37/0201* (2013.01); *C07C 29/48* (2013.01); *C07C 31/04* (2013.01)

(58) Field of Classification Search
CPC ... B01J 23/755; B01J 35/0006; B01J 37/0201
See application file for complete search history.

(56) References Cited

PUBLICATIONS

Lin et al., J. Physical Chemistry, (2013), v117, p. 17319-17326.*
Lin et al., ACS Appl Mater Interfaces, (2016), 8, 24238-24247.*
Chapter X: The oxidation of carbon Monoxide, Studies in Surface Science and catalysis, (1983), 15, 280-311.*
Ambrosetti, et al. "Enhanced chemical reactivity of graphene on a Ni(111) substrate" *J. Chem. Phys.* 144:111101 (2016) pp. 1-5.
Blöchl, P.E. "Projector augmented-wave method" *Phys. Rev. B* 50 (1994) pp. 17953-17979.
Bruix, et al. "A new type of strong metal-support interaction and the production of $H_2$ through the transformation of water on $Pt/CeO_2(111)$ and $Pt/CeO_x/TiO_2(110)$ catalysts" *J. Am. Chem. Soc.* 134 (2012) pp. 8968-8974.
Campbell, C.T. "The Degree of Rate Control: A Powerful Tool for Catalysis Research" *ACS Catal.* 7(2017) pp. 2770-2779.
Campbell, C.T. "Catalyst-support interactions: Electronic perturbations" *Nat. Chem.* 4 (2012) pp. 597-598.
Cui, et al. "Single layer graphene encapsulating non-precious metals as high-performance electrocatalysts for water oxidation" *Ener. Envir. Sci.* 9 (2016) pp. 123-129.
Dahal, et al. "Graphene-nickel interfaces: a review" *Nanoscale* 6 (2014) pp. 2548-2562.
Deng, et al. "Catalysis with two-dimensional materials and their heterostructures" *Nat. Nanotech.* 11 (2016) pp. 218-230.
Deng, et al. "Enhanced electron penetration through an ultrathin graphene layer for highly efficient catalysis of the hydrogen evolution reaction" *Angew. Chem. Int. Ed.* 54 (2015) pp. 2100-2104.
EIA. "Natural Gas Gross Withdrawals and Production" *U.S. Dept. of Energy* (2018) pp. 1-2.
Fei, et al. "General synthesis and definitive structural identification of $MN_4C_4$ single-atom catalysts with tunable electrocatalytic activities" *Nat. Catal.* 1 (2018) pp. 63-72.
Geim, et al. "The rise of graphene" *Nat. Mater.* 6 (2007) pp. 183-191.
Grimme, et al. "A consistent and accurate ab initio parametrization of density functional dispersion correction (DFT-D) for the 94 elements H—Pu" *J. Chem. Phys.* 132:154104 (2010) pp.
Grundner, et al. "Single-site trinuclear copper oxygen clusters in mordenite for selective conversion of methane to methanol" *Nat. Comm.* 6:7546 (2015) pp. 1-9.
Guan, et al. "Water oxidation on a mononuclear manganese heterogeneous catalyst" *Nat. Catal.* 1 (2018) pp. 1-8.
Guo, et al. "Greatly Enhancing Catalytic Activity of Graphene by Doping the Underlying Metal Substrate" *Sci. Rep.* 5:12058 (2015) pp. 1-7.
Henkelman, et al. "A fast and robust algorithm for Bader decomposition of charge density" *Comput. Mater. Sci.* 36 (2006) pp. 354-360.
Henkelman, et al. "A climbing image nudged elastic band method for finding saddle points and minimum energy paths" *J. Chem. Phys.* 113 (2000) pp. 9901-9904.
Henkelman, et al. "A dimer method for finding saddle points on high dimensional potential surfaces using only first derivatives" *J. Chem. Phys.* 111 (1999) pp. 7010-7022.
Heyden, et al. "Efficient methods for finding transition states in chemical reactions: comparison of improved dimer method and partitioned rational function optimization method" *J. Chem. Phys.* 123:224101 (2005) pp. 1-14.

(Continued)

*Primary Examiner* — Yong L Chu
(74) *Attorney, Agent, or Firm* — Dority & Manning, P.A.

(57) ABSTRACT

Disclosed are catalysts that include a doped atomic monolayer (e.g., graphene or hexagonal boron nitride) bonded to a nickel-based component. The dopant can be a transition metal or nonmetal dopant and the nickel-based component can be pure nickel (e.g., Ni(111)) or nickel/metal alloys. Also disclosed are processes for catalyzing reactions that include adsorbing a small molecule to the catalyst and contacting the adsorbed small molecule with a reactant. Catalyzed reactions include oxidation reactions including oxidation of methane to methanol, oxidation of carbon monoxide (e.g., in a PROX reaction).

17 Claims, 19 Drawing Sheets

(56) References Cited

PUBLICATIONS

Jin, et al. "Fabrication of a Freestanding Boron Nitride Single Layer and Its Defect Assignments" *Phys. Rev. Lett.* 102:195505 (2009) pp. 1-4.

Kirk, et al. "Theoretical Investigations of the Electrochemical Reduction of CO on Single Metal Atoms Embedded in Graphene" *ACS Cent. Sci.* 3 (2017) pp. 1286-1293.

Kresse, et al. "From ultrasoft pseudopotentials to the projector augmented-wave method" *Phys. Rev. B* 59 (1999) pp. 1758-1775.

Kresse, et al. "Efficiency of ab-initio total energy calculations for metals and semiconductors using a plane-wave basis set" *Comput. Mater. Sci.* 6 (1996) pp. 15-50.

Kresse, et al. "Efficient iterative schemes for ab initio total-energy calculations using a plane-wave basis set" *Phys. Rev. B* 54 (1996) pp. 11169-11186.

Kulkarni, et al. "Understanding Catalytic Activity Trends in the Oxygen Reduction Reaction" *Chem. Rev.* 118 (2018) pp. 2302-2312.

Latimer, et al. "Direct Methane to Methanol: The Selectivity-Conversion Limit and Design Strategies" *ACS Catal.* 8 (2018) pp. 6894-6907.

Latimer, et al. "Understanding trends in C—H bond activation in heterogeneous catalysis" *Nat. Mater.* 16 (2017) pp. 225-229.

Li, et al. "Stability and reactivity of copper oxo-clusters in ZSM-5 zeolite for selective methane oxidation to methanol" *J. Catal.* 338 (2016) pp. 305-312.

Machado, et al. "Graphene-based materials for catalysis" *Catal. Sci. Technol.* 2 (2012) pp. 54-75.

Monkhorst, et al. "Special Points for Brillouin-Zone Integrations" *Phys. Rev. B* 13 (1976) pp. 5188-5192.

Muntwiler, et al. "Determining adsorbate structures from substrate emission X-ray photoelectron diffraction" *Surf. Sci.* 472 (2001) pp. 125-132.

Narsimhan, et al. "Catalytic Oxidation of Methane into Methanol over Copper-Exchanged Zeolites with Oxygen at Low Temperature" *ACS Cent. Sci.* 2 (2016) pp. 424-429.

Neto, et al. "The electronic properties of graphene" *Rev. Mod. Phys.* 81 (2009) pp. 109-162.

Pacchioni, et al. "Charging of metal atoms on ultrathin MgO/Mo(100) films" *Phys. Rev. Lett.* 94:226104 (2005) pp. 1-4.

Pappas, et al. "Methane to Methanol: Structure-Activity Relationships for Cu—CHA" *J. Am. Chem. Soc.* 139 (2017) 14961-14975.

Perdew, et al. "Generalized gradient approximation made simple" *Phys. Rev. Lett.* 77 (1996) pp. 3865-3868.

Qiao, et al. "Single-atom catalysis of CO oxidation using $Pt_1/FeO_x$" *Nat. Chem.* 3 (2011) pp. 634-641.

Ravi, et al. "The Direct Catalytic Oxidation of Methane to Methanol—A Critical Assessment" *Angew. Chem. Int. Ed.* 56 (2017) pp. 16464-16483.

Rodriguez, et al. "Inverse Oxide/Metal Catalysts in Fundamental Studies and Practical Applications: A Perspective of Recent Developments" *J. Phys. Chem. Lett.* 7 (2016) pp. 2627-2639.

Romero-Muñiz, et al. "Substrate-induced enhancement of the chemical reactivity in metal-supported graphene" *Phys. Chem. Chem. Phys.* 20 (2018) 19492.

Saleheen, et al. "Liquid-Phase Modeling in Heterogeneous Catalysis" *ACS Catal.* 8 (2018) pp. 2188-2194.

Shan, et al. "Mild oxidation of methane to methanol or acetic acid on supported isolated rhodium catalysts" *Nature* 551 (2017) pp. 605-608.

Tauster, S.J. "Strong metal-support interactions" *Acc. Chem. Res.* 20 (1987) pp. 389-394.

Tomkins, et al. "Direct Conversion of Methane to Methanol under Mild Conditions over Cu-Zeolites and beyond" *Acc. Chem. Res.* 50 (2017) pp. 418-425.

Voiry, et al. "Enhanced catalytic activity in strained chemically exfoliated $WS_2$ nanosheets for hydrogen evolution" *Nat. Mater.* 12 (2013) pp. 850-855.

Wang, et al. "Heterogeneous single-atom catalysis" *Nat. Rev. Chem.* 2 (2018) pp. 65-81.

Wang, et al. "Oxidation energies of transition metal oxides within the GGA+U framework" *Phys. Rev. B* 73:195107 (2006).

Welborn, et al. "Computational optimization of electric fields for better catalysis design" *Nat. Catal.* 1 (2018) pp. 649-655.

Yan, et al. "Atomic engineering of high-density isolated Co atoms on graphene with proximal-atom controlled reaction selectivity" *Nat. Comm.* 9 (2018) pp. 3197.

Zhao, et al. "Theoretical Insights into the Selective Oxidation of Methane to Methanol in Copper-Exchanged Mordenite" *ACS Catal.* 6 (2016) pp. 3760-3766.

\* cited by examiner

OXIDATION BY USE OF ELECTRONIC ATOMIC MONOLAYER-METAL SUPPORT INTERACTION CATALYSTS

CROSS REFERENCE TO RELATED APPLICATION

This application claims filing benefit of Application Ser. No. 62/849,277, having a filing date May 17, 2019, which is incorporated herein by reference in its entirety.

FEDERAL RESEARCH STATEMENT

This invention was made with Government support under Contract No. OIA-1632824, awarded by the National Science Foundation (NSF). The Government has certain rights in the invention.

BACKGROUND

The need to develop more efficient catalysts has led to a search for new chemistries that can overcome deficiencies of existing catalysts. In general, the activity and selectivity of a catalyst can be modified by changing its composition or external environment. The effects of support, solvent, applied electric field, and strain can significantly regulate the properties of a catalyst and have been harnessed to achieve desired catalytic activity. The well-known strong metal-support interaction (SMSI) is a typical support interaction that usually includes the encapsulation of an active metal by a few-layer metal oxide support ($CeO_2$, $TiO_2$, etc.). Unfortunately, this encapsulation blocks the activity of the metal. Closely related to SMSI is the electronic metal-support interaction (EMSI), which is based upon the understanding that a metal catalyst experiences a favorable electronic perturbation by a metal oxide support that brings about higher activity.

The need for improved catalysts exists in a wide variety of applications. For instance, the increasing supply of natural gas and the cost differential between natural gas and petrochemicals that can be derived from natural gas make the development of efficient catalysts for transforming methane into value-added fuels and chemicals an appealing value proposition. Direct oxidation of methane to methanol (MTM) by use of molecular oxygen is the economically preferred approach for valorizing methane as compared to indirect oxidation processes involving the energy-intensive syngas production or the use of other, more expensive or corrosive oxidants. Unfortunately, despite active research for many decades, no economically viable direct MTM process has been developed on an industrial scale.

A prerequisite for a potential MTM catalyst is the ability to efficiently activate both methane and dioxygen. Computational studies have correlated the C—H activation barriers of methane with the hydrogen adsorption energies over various heterogeneous catalysts. The methane molecule is relatively inert and the C—H cleavage is difficult. The efficient activation of both $CH_4$ and $O_2$ at the same active site is even more challenging, explaining the lack of highly active MTM catalysts. While the reaction rate of the MTM catalyst can be increased with increasing reaction temperature, overoxidation occurs at high temperatures and optimal operating conditions have been suggested to be below 500K. Copper (Cu)-exchanged zeolites, mimicking methane monooxygenase that catalyzes MTM in nature, are among the most extensively explored low temperature MTM catalysts. Unfortunately, Cu-exchanged zeolites suffer from low activity and the active sites usually need to be pre-oxidized at high temperatures before the methane oxidation can take place. Meaningful but still unacceptably low MTM yields have been observed for mononuclear rhodium (Rh) species anchored on a zeolite or $TiO_2$ support and suspended in aqueous solution. Unfortunately, efficient MTM catalysts remain elusive.

Another example of an application that could benefit from improved catalysts is the preferential oxidation of carbon monoxide (CO) (PROX). Hydrogen produced through methane steam reforming and water gas-shift (WGS) reactions contains about 1% CO and must be further purified to reduce the CO concentration below 50 ppm for various applications, e.g., in proton-exchange-membrane fuel cells (PEMFCs). PROX is a promising cost-effective process for removal of CO as compared with CO methanation (CO+$3H_2 \rightarrow CH_4+H_2O$), which can consume up to 15% of the available $H_2$. A benchmark goal of 50/50 has been proposed for PROX catalysts, which means that the CO concentration in the product should be below 50 ppm, and the $O_2$ selectivity to $CO_2$ should be above 50%. Apart from the 50/50 goal, a good PROX catalyst should also have wide operating temperature window (e.g., about 353K to about 473K) and high thermal stability. Currently, platinum (Pt) group metal (PGM) and gold (Au)-based catalysts are the most extensively explored PROX catalysts. Pt catalysts typically possess high water stability, but the activity is low. To improve the activity of Pt catalysts, different preparation methods, oxide supports and promoters have been explored. A $Pt/Fe_2O_3$ PROX catalyst featuring sub-nanometer Pt clusters was found to be about 100 times more active than a commercially available $Pt/Al_2O_3$ catalyst. An inverse Pt-supported $Fe_1(OH)_x$ catalyst is reported to be about ten times more active than a $Pt/Fe_2O_3$ PROX catalyst. Other supported PGM catalysts, including iridium (Ir), ruthenium (Ru), and Rh, have also been explored as PROX catalysts. Au catalysts exhibit high PROX activity, but the selectivity to $CO_2$ decreases with increase in temperature due to the oxidation of $H_2$. A single-atom $Au/CeO_2$ catalyst was found to suppress the oxidation of $H_2$, but it still suffers from a drop in $CO_2$ selectivity after 20 hours of operation. Apart from the activity loss of the catalyst, the presence of water can significantly affect the performance of Au catalysts. A recent study suggests that a commercial $Au/Al_2O_3$ catalyst exhibits optimal performance when two monolayers of water are adsorbed on the catalyst surface.

Despite progress in MTM, PROX, and other catalysts, cost-effective catalysts with high activity are still rare. What are needed are improved catalysts that can be used for efficient conversions.

SUMMARY

According to one embodiment, disclosed is a catalyst that includes a doped atomic monolayer. For instance, an atomic monolayer can be a graphene-based monolayer or a hexagonal boron nitride-based monolayer that can be doped with a transition metal or another useful single atom dopant doped into the lattice of the atomic monolayer. In addition, the catalyst can include a component bonded to the atomic monolayer at a surface of the component, the component including nickel. For instance, the component can be a bulk substrate and the atomic monolayer can be bonded to a surface of the substrate. Alternatively, the component can be particulate and the particulate can be bonded to a surface of the atomic monolayer.

According to one embodiment, disclosed is a method for catalyzing a reaction. A method can include adsorbing a small molecule to a catalyst, the catalyst can include a doped atomic monolayer and a component that includes nickel bonded to the doped atomic monolayer. A method can also include contacting the adsorbed small molecule with a reactant, upon which a reaction occurs involving the reactant and the small molecule and thereby forming a reaction product. For instance, a small molecule including oxygen can be adsorbed (e.g., $O_2$, OH) and a reaction can oxidize a reactant (e.g., methane ($CH_4$), carbon monoxide (CO), ethylene ($C_2H_4$)).

Methods and catalysts can beneficially be utilized in oxidation reactions including MTM reactions, PROX reactions, and ethylene oxidation reactions, among others.

BRIEF DESCRIPTION OF THE FIGURES

A full and enabling disclosure of the present invention, including the best mode thereof to one skilled in the art, is set forth more particularly in the remainder of the specification, which includes reference to the accompanying figures, in which.

Figure 1:
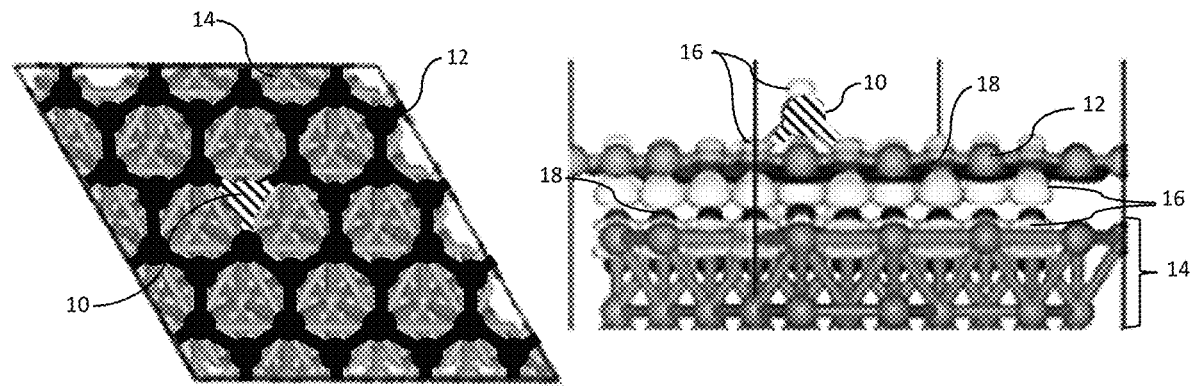
FIG. 1 presents a top view (left) and side view (right) of a Rh-doped graphene (Rh-GR) supported on nickel (111) (Rh-GR/Ni(111)). The side view displays a charge difference plot upon adsorption of the Rh-GR on the Ni(111) as denoted by lighter and darker spheres.

Repeat use of reference characters in the present specification and drawings is intended to represent the same or analogous features or elements of the present invention.

DETAILED DESCRIPTION

Reference now will be made to embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only and is not intended as limiting the broader aspects of the present invention, which broader aspects are embodied exemplary constructions.

Disclosed are catalysts for oxidation of targeted reactants. More specifically, disclosed catalysts can utilize an electronic atomic monolayer-metal support interaction (EAMSI) that enables the controlled activation of an adsorbed small molecule such as dioxygen. The controlled activation of the small molecule can in turn lead to controlled activation of a targeted reactant through an Eley-Rideal reaction mechanism. Disclosed catalysts include a nickel-basedmetal component and a doped atomic monolayer. Without wishing to be bound to any particular theory, it is believed that the metal component can be utilized to regulate the adsorption energy of small molecules adsorbed on or near the dopant of the doped atomic monolayer. As such, it is possible to tune the properties of the catalysts by identifying and harnessing EAMSI that can be used to modify the adsorption strength of intermediate and TS structures and thus provide high efficiency conversion of reactants to desired reaction products. For instance, due to favorable electrostatic interactions, over-activation of a desired reaction product (e.g., methanol) can be inhibited, improving efficiency of the targeted reaction (e.g., an MTM oxidation reaction). The diversity of atomic monolayers, dopants, and content and morphology of nickel-based metal components, as may be utilized in forming the catalysts, can provide for design of a large variety of single atom catalysts (SACs) for any number of useful applications.

The atomic monolayer of disclosed catalysts can be based on any of a number of materials known in the art possessing an essentially planar lattice a tan atomic-level thickness. Also referred to as two-dimensional (2D) sheets or crystals, these materials have attracted widespread interest in a variety of applications and fields including photo-electricity as well as for use as catalysts and transistors. Atomic monolayers can exhibit many desirable characteristics such as high specific surface area and high Young's modulus. Examples of atomic monolayers as may be incorporated in disclosed catalysts can include, without limitation, graphene (GR), hexagonal boron nitride (h-BN), silicene, germanium monosulfide (GeS), molybdenum disulfide ($MoS_2$), and phosphorene. In general, the atomic monolayer of the catalyst can have few if any grain boundaries. For instance, in one embodiment, the atomic monolayer can be a single crystal monolayer with no grain boundaries.

In one embodiment, the atomic monolayer can be formed from GR or hBN atomic monolayers, which are one-atom-thick planar sheets of sp2-bonded carbon atoms or boron nitride atoms, respectively, that are densely packed into a ring structure in a planar crystal lattice.

The catalysts include a single atom dopant that is immobilized in the lattice of the atomic monolayer. The immobilized dopant can be considered a single-atom catalyst, which is a recently emerging frontier in heterogenous catalysis that promises very high atom efficiency. Any dopant capable of being immobilized in the lattice of the atomic monolayer can be utilized, which can provide for the design of highly selective heterogeneous catalysts with high uniformity of active sites.

Exemplary dopants can include, without limitation, transition metals, alkali metals, post-transition metals, metalloids or non-metal such as, and without limitation to nitrogen (N), phosphorous (P), and fluorine (F). By way of example, and without limitation, transition metal dopants as may be incorporated in an atomic monolayer can include scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), or mercury (Hg). In some embodiments, a transition metal dopant can be selected from Mn, Fe, Cu, Rh, and Ir. In one embodiment, a transition metal dopant can be Rh. Other dopants of interest can include, without limitation, boron (B), lithium (Li), nitrogen (N), and potassium (K).

Methods for forming doped atomic monolayer sheets are generally known in the art, and the disclosed catalysts are not limited to any particular formation methods for incorporating a dopant into the lattice of an atomic monolayer. By way of example, and without limitation, in one embodiment, a doped atomic monolayer can be formed by exposing an intermediate of the atomic monolayer, e.g., a non-doped graphene film to a gas that includes the dopant; exciting a plasma within a chamber containing the intermediate atomic monolayer and the doping gas (e.g., a sealed vacuum oven under about 3000° C. and argon gas); and low-energy ion beam implantation of the dopant of the gas into the lattice of the atomic monolayer. In some embodiments, a chemical vapor deposition (CVD) process, as is generally known in the art, can be utilized to form a doped atomic monolayer in a single-step formation.

When considering an atomic monolayer that includes multiple different elements in the sheet, e.g., hBN, the insertion site of the dopant can be varied, which can be utilized to control catalyst characteristics. For example, when forming a catalyst that includes a doped hBN atomic monolayer, a boron vacancy can be preferred over a nitrogen vacancy, and as such, the dopant atom can be immobilized in the atomic monolayer utilizing a B-defective hBN intermediate. Alternatively, the dopant can be inserted at a nitrogen vacancy of an hBN atomic monolayer in other embodiments. Similarly, an atomic monolayer intermediate of other materials (e.g., GeS) can be formed or provided to include particular defects for insertion of the dopant of choice at a desired, predetermined location in the lattice of the atomic monolayer.

The metal component of the catalysts can include nickel alone or a multi-component component that includes nickel alloyed with one or more additional metals at a surface. Ni-based multicomponent materials can include any suitable metal or combination of metals, and selection thereof can be utilized to modify or control characteristics of the metal component, e.g., lattice parameters of the metal component, electronic properties of the metal component, etc. which can in turn be used to modify or control catalytic properties of the catalyst.

By way of example and without limitation, in one embodiment, a nickel-based component can include nickel in combination with one or more additional transition metals, e.g., one or more of Sc, Ti, V, Cr, Mn, Fe, C, Cu, Zn, Y, Zr, Nb, Mo, Tc, Ru, Rh, Pd, Ag, Cd, Hf, Ta, W, Re, Os, Ir, Pt, Au, or Hg. A multi-metal nickel-based component is not limited to combination of nickel with a transition metal, and metals of a multi-metal component can encompass any metal as is known including, without limitation, alkali metals, alkaline earth metals, transition metals, post-transition metals, metalloids, lanthanoids, and any combination thereof. For instance, in one embodiment, a nickel-based component can include nickel in combination with one or more of Pt, Pd, Au, Cu, Ag, Ir, Co, Rh, Ru, La, Mg, Ca, Sr, Ba, Li, Na, K and Mn. In addition, while multi-metal nickel-based components can encompass a bimetal component or a tri-metal component in some embodiments (e.g., Ni/Co/Rh, Ni/Co/Ru, Ni/Co/Pt, Ni/Co/Ce, Ni/Co, Ni/Ru, Ni/Pt), the nickel-based component is not limited to such, and any number of metals can be incorporated in a nickel-based component. In general, the nickel-based component can include from about 50 at. % to 100 at. % nickel. In some embodiments, the various metals can be present in a multi-metal nickel-based component in equal amounts. In other embodiments, different metals can be present in a component in different amounts; for instance, a multi-metal nickel based component can include nickel in a majority amount as compared to all other metals of the component (i.e., greater than 50 at. % nickel with the remainder formed of one or a plurality of other metals).

The lattice structure of the metal component is not critical and can be modified to improve activity of the catalyst. For instance, in one embodiment, the lattice structure of the metal component can be designed or selected to exhibit a small mismatch with the lattice of the atomic monolayer bonded thereto. By way of example, in one embodiment, Ni(111) can form the nickel-based metal component. Ni(111) exhibits a lattice constant of about 2.49 Å, which is a small mismatch to those of both GR (2.46 Å) and hBN (2.51 Å). A relatively small lattice mismatch between the atomic monolayer and the nickel-based component can improve bonding and electronic interaction between the two, in some embodiments. It should be understood, however, that a nickel-based component formed solely of nickel is not limited to Ni(111) and other lattice parameters of a nickel component are encompassed herein. In one embodiment, inclusion of additional metal(s) in the nickel-based component can be utilized to modify the lattice parameter(s) of the component; for instance, so as to modify or control catalytic properties of the catalyst.

The morphology of the nickel-based component is not particularly limited, and in one embodiment, this aspect of the catalysts can be utilized to modify or control properties of the catalysts. In one embodiment, the doped atomic monolayer component can be supported on a nickel-based substrate. For instance, a support of any useful size, which can vary depending upon the specific application, can include the nickel-based component at least at a surface of the support (e.g., as an upper layer of a support or throughout the entire depth of the support). A doped atomic monolayer can then be adsorbed at the Ni-containing surface.

In one embodiment, the Ni-containing component can be a particulate, and during formation of the catalyst, the Ni-containing particulate can be adsorbed at a surface of the atomic monolayer.

The particles of an Ni-based component can be of any suitable size and shape. In one embodiment, the particles of a Ni-based component can be microparticles or nanoparticles. As used herein, the prefix "nano" refers to the nanometer scale (i.e., from about 1 nm to about 999 nm). For example, particles having an average diameter on nanometer scale (i.e., from about 1 nm to about 999 nm) are referred to as "nanoparticles." Particles having a size of greater than 1,000 nm (i.e., 1 □m) are generally referred to as "microparticles," since the micrometer scale generally involves those particles having an average diameter of greater than 1 □m. In addition, while the particulate can have a narrow size distribution in some embodiments, this is not a requirement, and a particulate can include particles of different sizes in other embodiments.

Particles of a nickel-based particulate can have any suitable shape including, without limitation, sphere, cubic, rod, star, polyhedral, amorphous (i.e., ill-defined or arbitrary), or any combination thereof. In some embodiments, a particulate can include particles of only a single shape. In other embodiments, particles of a particulate can include combinations of shapes of the individual particles forming the particulate.

Independent of the morphology of the Ni-based metal component, the doped atomic monolayer and the Ni-based metal component can be adsorbed to one another during formation of a catalyst. In general, the adsorption between the two can be a chemisorption, in which bonds, e.g., covalent bonds, can be formed between the Ni-based metal component and the doped atomic monolayer. Without wishing to be bound to any particular theory, it is believed that covalent chemical bonding between the metal component and the atomic monolayer can encourage transfer of charge from the metal component to the atomic monolayer, which can then be available to activate an adsorbed small molecule and a reactant during a catalyzed oxidation process.

Chemisorption between the metal component and the atomic monolayer can be carried out according to known processes, such as sintering processes as are known in the art. For instance, a sintering process can include contact between an atomic monolayer and a metal component in an air free environment at elevated temperatures, optionally in the presence of an activation species, to form a bond (e.g., a carbide bond in the case of graphene) between the two. In some embodiments, the atomic monolayer can be formed directly on the metal substrate, either in conjunction with or prior to doping of the atomic monolayer, which formation process can likewise form a chemical bond between the atomic monolayer and the metal component. In one embodiment, a metal component can be encapsulated by an atomic monolayer, a chemical vapor deposition process in mesoporous silica, as described by Cui, et al. (Single layer graphene encapsulating non-precious metals as high-performance electrocatalysts for water oxidation. Energy Environ. Sci. 2016, 9, 123-129).

During use, a small molecule can be adsorbed to a surface of a catalyst. Disclosed catalysts are understood to encourage an oxidation reaction according to an Eley-Rideal reaction mechanism, in which a first reactant (generally the small molecule reactant) is chemisorbed to a surface of the catalyst, and a second reactant is not chemisorbed to the surface of the catalyst. As utilized herein, the term "small molecule" generally refers to a molecule having a molecular weight of about 1000 daltons or less.

In one embodiment, the chemisorbed small molecule can be a reactant that will be reduced during the catalyzed reaction, and the non-chemisorbed reactant can be oxidized during the catalyzed reaction.

Exemplary small molecules can include, without limitation, oxygen, hydroxyl-containing small molecules, methoxy-containing small molecules, and those including multiple reactivities, e.g., —O, —OH, and/or —OCH$_3$.

Adsorption of the small molecule reactant to the surface of the catalyst can be carried out through contact of the two; for instance, contact at increased temperature of from about 320K to about 500 K.

In one embodiment, disclosed catalysts can be utilized in catalyzing an MTM reaction. In this embodiment, a small molecule including oxygen (e.g., $O_2$) can be adsorbed to the surface, and following or concurrent with this adsorption, the surface can be contacted with methane. Disclosed catalysts can exhibit a high activity for methane partial oxidation, which can be traced to the presence of the adsorbed oxygen on the surface. During a reaction procedure, the adsorbed oxygen can be activated by the dopant atom (e.g., Rh) and graphene C atoms. As discussed further in the examples section, the EAMSI of the catalyst can lead to breaking of the conventional C—H activation scaling relationship that predicts a transition state energy difference of ~0.55 eV between $CH_4$ and $CH_3OH$, leading to a significantly narrowed energy difference. The breaking of the scaling relationship is understood to be due to the synergy of the adsorbed activated oxygen atoms on the surface and a neighboring cationic doping atom that electrostatically attracts the methane carbon atom in the C—H transition state and repels the methanol carbon atom, a mechanism that can encourage minimal overoxidation of methanol.

In one embodiment, a catalyst as disclosed herein can be designed as a PROX catalyst that can harness the electronic atomic monolayer-metal support interaction between the doped monoatomic layer and the metal component. In one embodiment of a PROX catalyst, an oxygen containing small molecule, e.g., $O_2$ can be adsorbed on a catalyst including a nitrogen-doped graphene and a Ni(111) component, upon which the O—O bond can dissociate. The adsorbed atomic oxygen can subsequently react with CO or $H_2$.

Beneficially, a PROX catalyst as described can maintain activity in the presence of water, which has been a serious issue for previously known PROX catalysts. Microkinetic modelling of PROX catalysts discussed further herein suggests that the turnover frequency of $O_2$ consumption with a CO partial pressure of 0.01 bars can be over 2/s at room temperature and the selectivity to $CO_2$ can be about 100%.

Disclosed catalysts can be beneficially utilized in a large variety of reaction schemes, in addition to MTM and PROX catalysis. For instance, disclosed catalysts can be utilized in ethylene oxidation, and as oxygen reduction reaction (ORR) catalysts, among others.

Beneficially, disclosed catalysts can activate the reactants at low temperatures, e.g., from about 350K to about 500K in some embodiments, which can prevent over-oxidation of reaction products, as well as lower processing costs. In addition, disclosed catalysts can be designed to activate only targeted reactants, e.g., activation of reaction products can be thermodynamically unfavorable, which can further prevent over-oxidation of reaction products. Disclosed catalysts can also overcome issues of typical of MTM catalysts, e.g., previously known Cu-exchanged zeolite catalysts such as the necessity of catalyst pre-oxidation, low activity, and methane conversion, as well as strong adsorption of methanol.

As a result of activation control possible by design and use of disclosed catalysts, the catalysts can provide for highly efficient reaction processes. For instance, high single-pass conversions can be attained by use of disclosed catalysts, and multiple recycle of product streams through the reaction process can be avoided. For instance, in one embodiment, a PROX catalyst can be provided that can meet or exceed the 50/50 goal of a PROX system in CO conversion of a stream comprising hydrogen and CO. Moreover, in one embodiment, a 50/50 goal can be met or exceeded in a single pass.

The present disclosure may be better understood with reference to the Examples set forth below.

EXAMPLES

Methods

First-principles calculations were performed using periodic density functional theory (DFT) as implemented in the Vienna Ab initio Simulation Package (VASP 5.4.4). The spin-polarized generalized gradient approximation (GGA) with the PBE functional was used to treat exchange-correlation effects. A plane wave basis set with a cutoff energy of 400 eV was selected to describe the valence electrons. The energy difference between reaction energies computed with a 400 and 500 eV cutoff were found to be smaller than 5 meV.

The electron-ion interactions were described by the projector augmented wave (PAW) method. The Brillouin zone integration was performed with a 3×3×1 Monkhorst-Pack45 (MP) k-mesh and Gaussian smearing ($\sigma$=0.1 eV). Grimme's DFT-D346 scheme was used to include the van der Waals interactions semi-empirically.

The SCF and force convergence criteria for structural optimization were set to $1\times10^{-5}$ eV and 0.01 eV/A, respectively. The climbing image nudged elastic band (CI-NEB) and dimer methods were used to optimize the transition state structures. The force convergence criterion for transition state optimization was set to be 0.03 eV/A. Transition states were confirmed with existence of one imaginary frequency whose corresponding eigenvector points in the direction of the reactant and product state.

A five-layer 4×4 Ni(111) slab was used to describe the Ni slab and neighboring slabs were separated by a 13 Å vacuum. The lattice parameter of Ni(111) is close to that of graphene (Ni(111), 2.49 Å; graphene, 2.46 Å). To construct a Ni(111) supported graphene, the lattice parameter of Ni(111) was adopted. Harmonic transition state theory was used to calculate all elementary rate constants of surface processes. Collision theory with a sticking coefficient of 1 was used to estimate the rate constants for adsorption processes. The energy of $O_2$ was increased by 0.49 eV to correct the overbinding of O—O predicted by the PBE functional.

The adsorption energy of a gas phase molecule was defined as:

$$E_{ads}=E(\text{surface+adsorbent})-E(\text{surface})-E(\text{adsorbent}).$$

The adsorption energy of a metal atom was defined as:

$$E_{ads}=E(\text{surface+atom})-E(\text{surface})-E(\text{atom from bulk metal})$$

Example 1

The adsorption of Rh-doped (4×4) graphene (GR-Rh) on (4×4) Ni(111) support 14 is illustrated in FIG. 1 including a top view (left) and a side view (right). A Rh atom 10 can be immobilized at the single vacancy of a graphene sheet 12 with an adsorption energy ($E_{ads}$) of −1.90 eV. The $E_{ads}$ of GR-Rh on (4×4) Ni(111) was calculated to be −3.52 eV.

Figure 4:
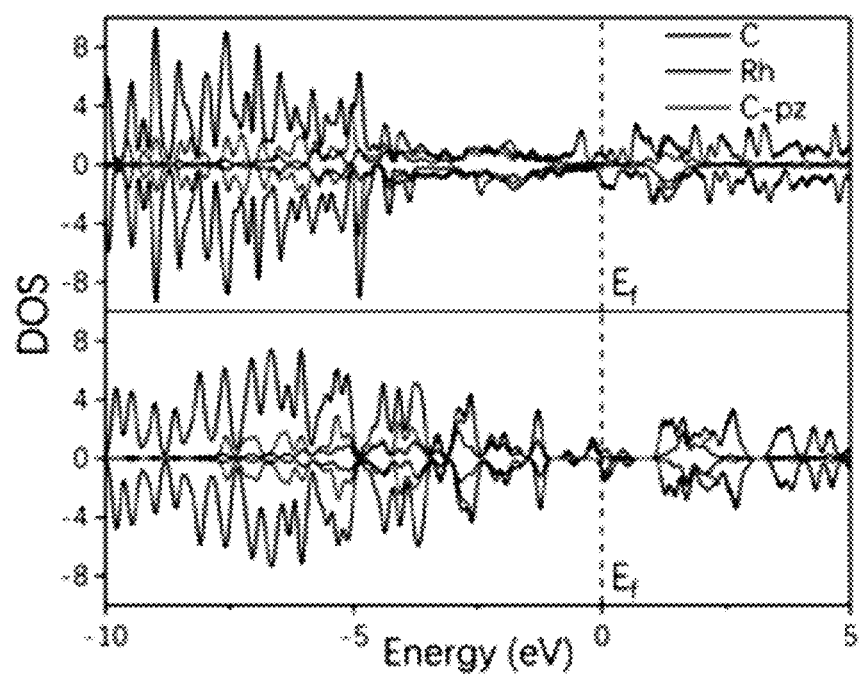
FIG. 4 presents a projected density of states (DOS) of carbon (C) and Rh for Rh-GR supported on Ni(111) (top) and unsupportedRh-GR (bottom).

The side view on FIG. 1 includes the charge different plot upon the adsorption of GR-Rh on the surface of the Ni(111) substrate. The isosurface value is 0.003 |e|/bohr$^3$. The accumulation and depletion of electrons is indicated in FIG. 1 by the lighter (accumulation) 16 and darker (depletion) 18 areas. The covalent interaction between GR-Rh and Ni(111) was reflected by significant charge accumulation between GR-Rh and Ni(111), as indicated in FIG. 1, and a downshift of the GR-Rh projected density of states (DOS) for GR-Rh supported on Ni(111) as compared with freestanding GR-Rh (FIG. 4).

Figure 2:
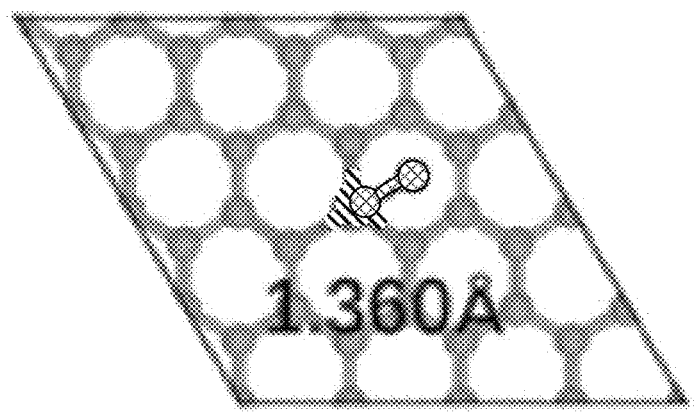
FIG. 2 schematically illustrates the adsorption of dioxygen ($O_2$) on free-standing Rh-GR.
Figure 3:
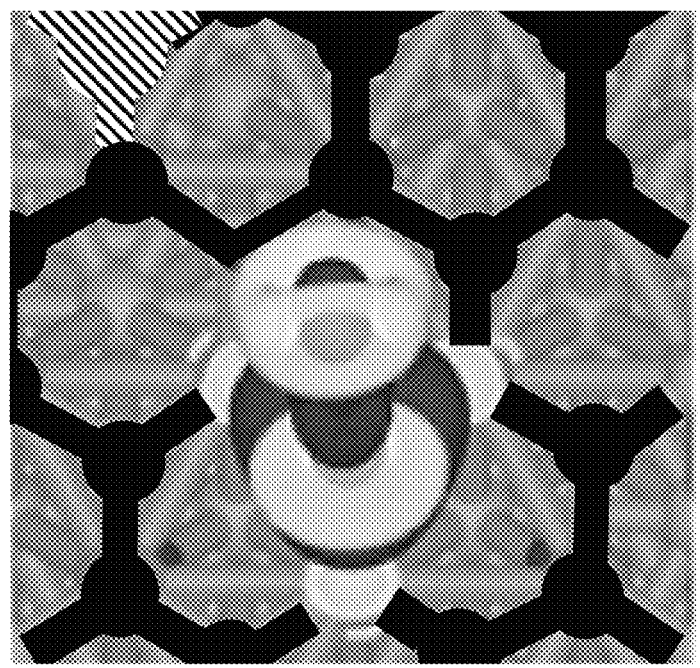
FIG. 3 presents a charge difference plot upon the adsorption of $O_2$ onto Rh-GR on Ni(111).
Figure 5:
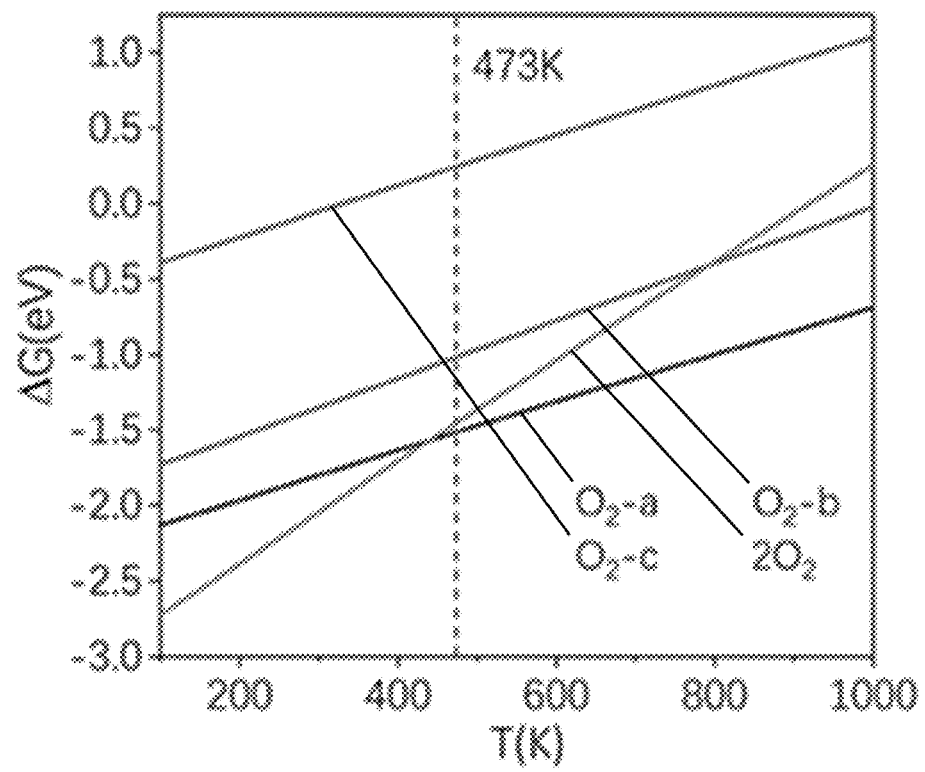
FIG. 5 presents results from constrained thermodynamic calculations of $O_2$ adsorption on Rh-GR/Ni(111) at various orientations. The $O_2$ partial pressure is 1 bar. O—O bond lengths are labeled for each representation.
Figure 5:
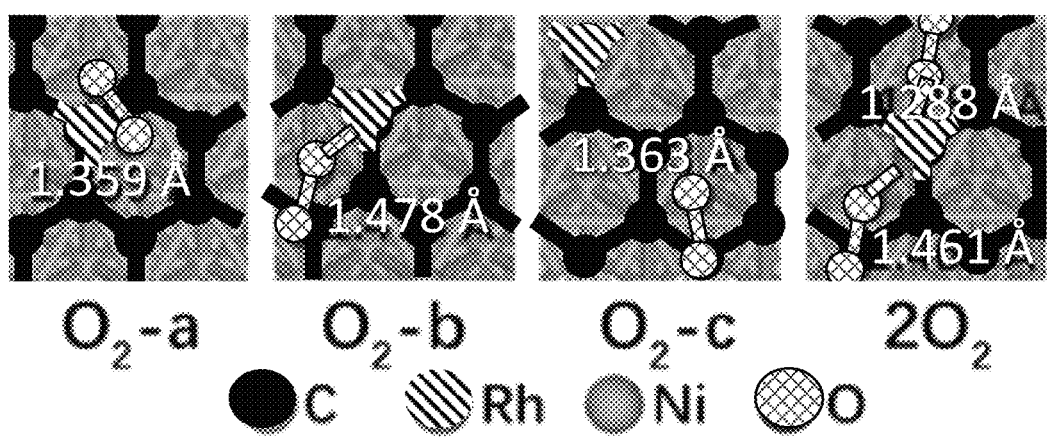

Bader charge calculations suggest that the GR—Rh layer composed of $C_{31}Rh$ gained 1.58 |e⁻| from the Ni(111) support. The adsorption of one $O_2$ to the GR—Rh layer as schematically illustrated in FIG. 3 was examined at several different sites on a GR-Rh sheet including at the Rh site ($O_2$-a), GR-Rh interfacial site ($O_2$-b), and GR basal plane site ($O_2$-c) (FIG. 5). The $O_2$ chemisorption energies for each site are −2.34, −1.99 and −0.60 eV, respectively. At the $O_2$-b interfacial site, the O—O bond length is elongated to 1.478 Å, as compared with the gas phase bond length of 1.234 Å. GR-Rh supported on Ni(111) can also accommodate another $O_2$ molecule in close vicinity of Rh ($2O_2$; FIG. 5) with a total adsorption energy of −3.15 eV. In contrast, $O_2$ can only be adsorbed on the Rh site of freestanding GR-Rh with an adsorption energy of −2.03 eV, and no C—O bond can be formed as schematically illustrated in FIG. 2. Bader charge calculations suggest that the $O_2$ of the configuration $O_2$-c (FIG. 5) gains 0.72|e⁻| upon adsorption while charge redistributes at the C bonded to the 0 atoms as well as the three nearest-neighboring C atoms. The energetically favorable charge redistribution originates from the delocalized C $p_z$ orbitals of GR-Rh supported on Ni(111) near the Fermi level, which are absent for unsupported GR-Rh such that the electron donation from the non-bonded C to $O_2$ is hindered.

Constrained thermodynamics calculations were performed to examine the stability of adsorbed oxygen at various temperatures and pressures. At an oxygen partial pressure of 1 bar and, a typical operating temperature of 473K, it was found that $O_2$-a was the most stable adsorption configuration, which was 0.06 eV more stable than $2O_2$. $O_2$-c was not stable at MTM operating conditions. However, a chemisorbed $O_2$ that is activated to a greater extent might be more active for $CH_4$ activation, the $O_2$-a, $O_2$-b, and $2O_2$ structures were considered as active sites for the MTM process.

Figure 6:
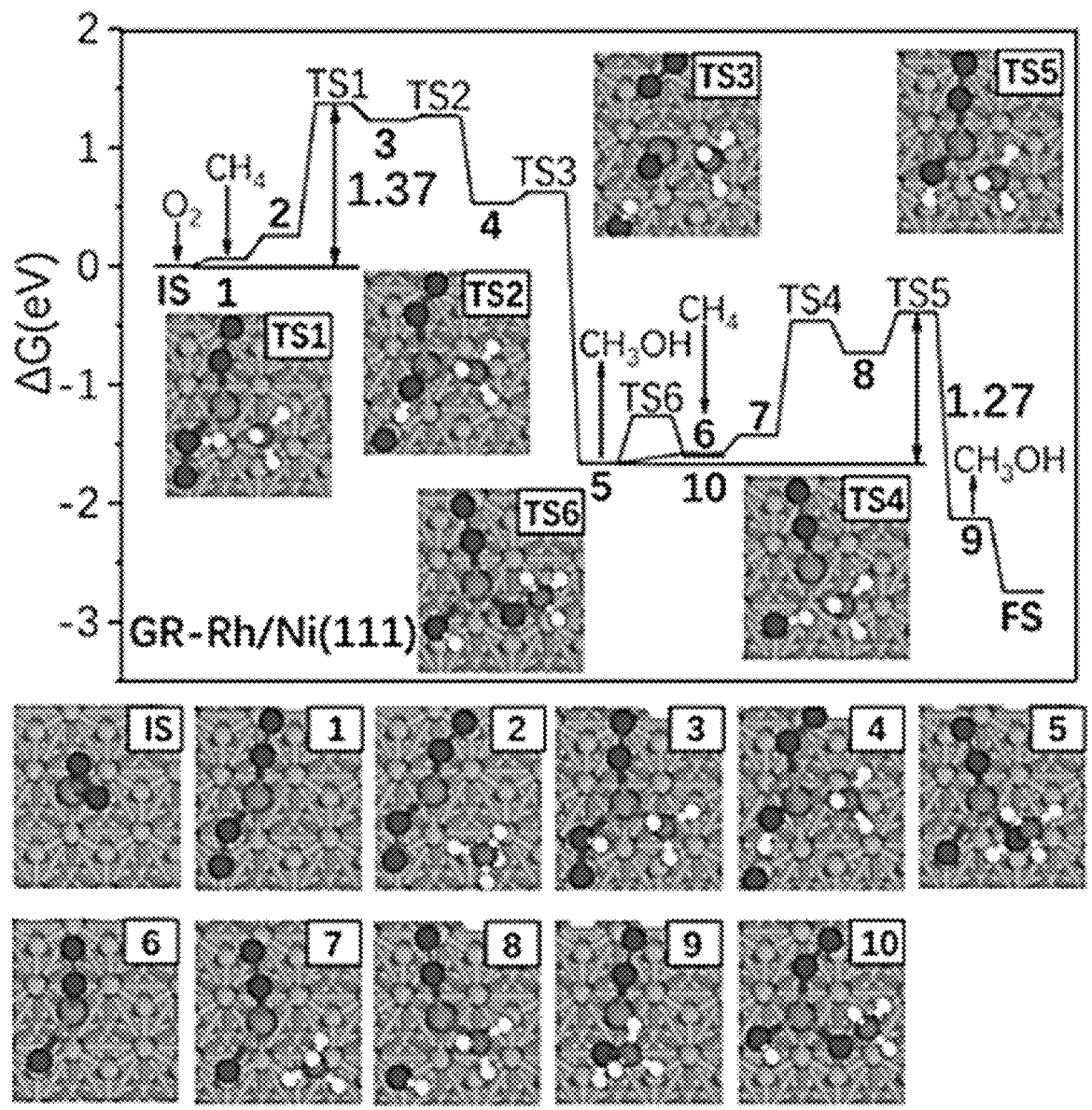
FIG. 6 provides pressure corrected ($P_{O2}$=1 bar, $P_{CH4}$=50 bar, $P_{CH3OH}$=1 bar) free energy at 473K associated with the configurations of each intermediate and transition state for the $CH_4$ partial oxidation over Rh-GR/Ni(111). The $2O_2$ configuration is the active species. IS and FS denote initial and final state, respectively.
Figure 7:
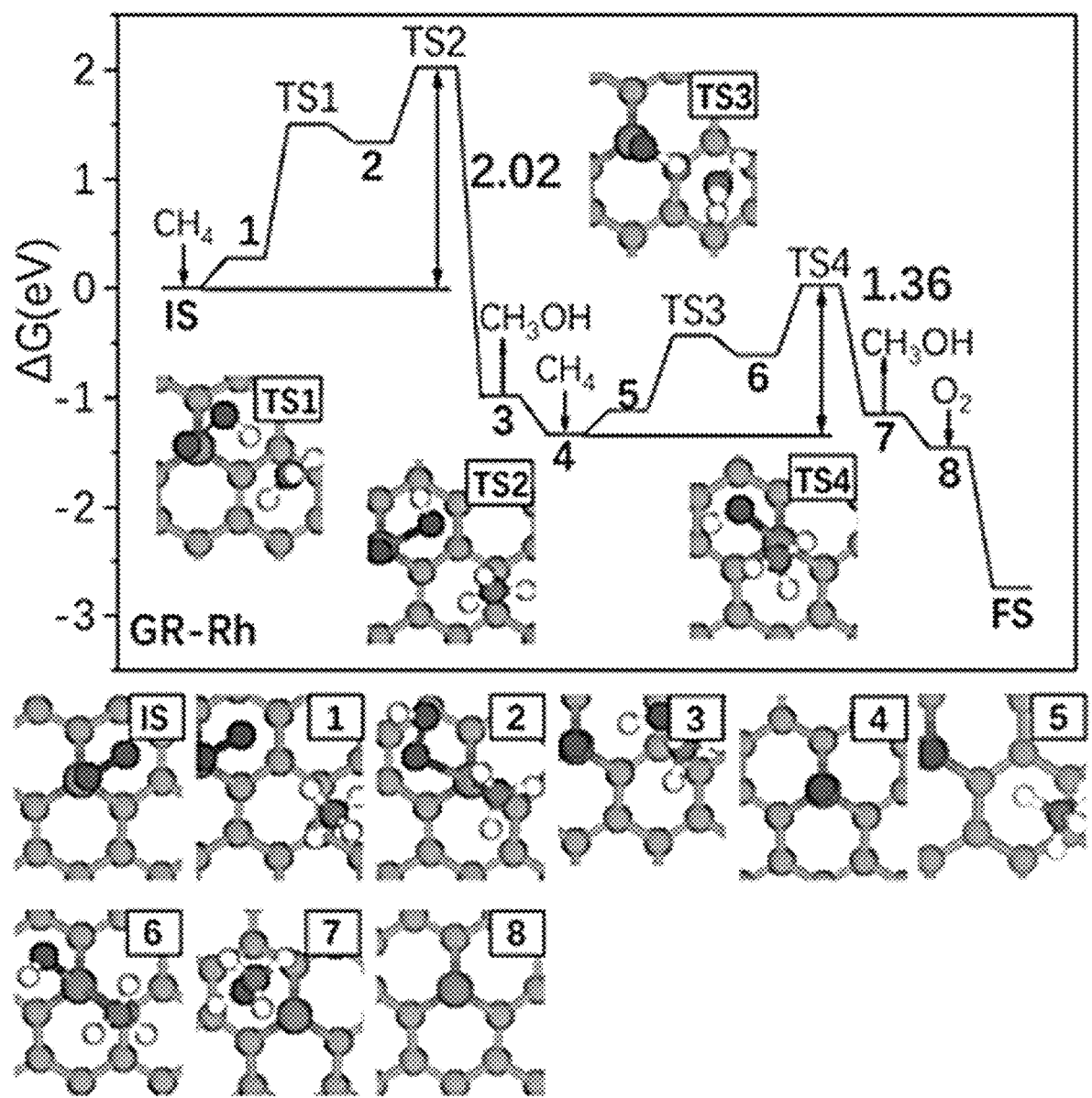
FIG. 7 provides pressure corrected ($P_{O2}$=1 bar, $P_{CH4}$=50 bar, $P_{CH3OH}$=1 bar) free energy at 473K associated with the configurations of each intermediate and transition state for the $CH_4$ partial oxidation over unsupported Rh-GR. The $2O_2$ configuration is the active species. IS and FS denote initial and final state, respectively.

Reaction energy profiles of methane oxidation on GR-Rh supported on Ni(111) (GR-Rh/Ni(111)) with $2O_2$ as the active site is shown in FIG. 6 and FIG. 7. For the calculation of the free energy profiles, the partial pressures of $CH_4$, $O_2$, and $CH_3OH$ were set to 50, 1, and 1 bar, respectively. The temperature was set to 473 K.

Starting from $O_2$-a (IS, FIG. 6), one additional $O_2$ is adsorbed to form the active site (1), which is endergonic by 0.06 eV. Next, methane physisorbs on GR-Rh/Ni(111) (2), which subsequently can react with the two oxygen atoms of the adsorbed $O_2$ with a bond length of 1.461 Å (while the other adsorbed $O_2$ with an 0-0 bond length of 1.288 Å is a bystander during the reaction). For the reaction with the first oxygen atom, breaking of the C—H bond occurs concurrently with formation of an O—H bond on GR-Rh/Ni(111), the formation of a Rh—C bond, and a further elongation of the O—O bond to 1.505 Å (2→3). The first reaction step occurs with a reasonably low free energy barrier of 1.12 eV (FIG. 6). The breaking of the O—O bond (3-4) only requires overcoming a small barrier of 0.04 eV. The formation of the first $CH_3OH$ (4→5) also occurs readily with a free energy barrier of 0.09 eV, which can be explained by the high exergonicity of this elementary step (−2.19 eV). Subsequent desorption of $CH_3OH$ is slightly endergonic by 0.08 eV (5→6), significantly facilitating the often-challenging methanol removal step typical of Cu-exchanged zeolites. The second oxygen then reacts with another $CH_4$ by overcoming a free energy barrier of 0.96 eV (7→8). The second $CH_3OH$ is formed upon association of the $CH_3$ and OH species (8→9). Finally, upon the desorption of the second $CH_3OH$ (9→FS), the catalytic cycle is closed.

Apart from the methanol formation mechanism, 0-H bond breaking of the adsorbed methanol can also occur (5→10), forming an adsorbed methoxy and hydroxyl that in some catalyst systems (see below)—but not on GR-Rh/Ni(111) as shown in FIG. 6—can poison the active site. The entire MTM process has an effective barrier of 1.37 eV, corresponding to the first $CH_4$ activation process. As $CH_4$ is only physiosorbed at the active center with pre-adsorbed $O_2$/O, the MTM mechanism can be described as an Eley-Rideal mechanism.

The energy profile of the MTM process occurring at $O_2$-b, which features a chemisorbed $O_2$ at the interfacial site with an O—O bond length of 1.478 Å (FIG. 5) was also examined. While the methane C—H activation and the formation of methanol can readily occur, the effective barrier of the reaction amounts to 1.62 eV since the free energy of the $O_2$-b site is 0.50 eV higher than that of $O_2$-a. Starting from $O_2$-a, where $O_2$ is adsorbed over Rh, both the first methane C—H cleavage and the methanol formation step are difficult with an effective barrier of 1.74 eV. The high barrier can be explained by two aspects: 1) the $O_2$ of $O_2$-a is activated to a lesser extent than that at an interfacial site and there is an energy penalty to further reduce $O_2$; and 2) $O_2$ binds with Rh strongly and $CH_3$ has to compete with $O_2$ for the adsorption site. Since the high effective barrier of the first methanol formation process for $O_2$-a is even higher than that of $O_2$-b, the second methanol formation process for $O_2$-a was not examined.

Interestingly, the $CH_4$ activation process is dramatically different for freestanding GR-Rh (FIG. 7). An $O_2$ molecule only binds with Rh through a $n^2$ mode and the O—O bond length is elongated to 1.360 Å upon adsorption (FIG. 2). The effective barrier of the entire process was calculated to be 2.02 eV, which occurs at the formation of the first methanol elementary step (2→3). The very different free energy profile of the Ni(111)-supported and freestanding GR-Rh highlights the role of the metal support for the MTM reaction.

As Cu-exchanged zeolites are among the most extensively explored catalysts for MTM conversion, Cu was also examined for TM-doped GR supported on Ni(111) as a candidate of an MTM catalyst. Preferred $O_2$ adsorption configurations under reaction conditions were determined by constrained thermodynamics calculations. With the most stable configuration of two $O_2$ adsorbed on GR-Cu/Ni(111), it was found that the effective barrier of the first C—H cleavage was 1.62 eV, significantly higher than the effective barrier of 1.37 eV for the entire process on GR-Rh/Ni(111). An energy barrier difference of 0.25 eV suggests a ~460 times lower reaction rate at 473K.

The energy profile of the MTM on Rh-doped hexagonal boron nitride (hBN) was also examined. Three $O_2$ can adsorb neighboring Rh dopant at operating conditions. While methane activation and methanol formation can occur on hBN-Rh/Ni(111) with an effective barrier of only 1.31 eV, methoxy species can be formed easier than methanol and is highly stable, rendering the effective barrier of the second methanol formation step to be 2.05 eV and poisoning the catalyst.

Owing to the electronic perturbation of the Rh-doped GR monolayer by the presence of the Ni(111) support, impressive catalytic activities for methane partial oxidation were predicted that are non-existent for the free-standing counterparts. The interaction between the Rh-doped GR and Ni(111) that enables the catalytic properties of Rh-doped GR is termed as Electronic Atomic Monolayer-metal Support Interaction (EAMSI) which is distinct to the classical strong metal-support interactionor electronic metal-support interaction. The previously reported electronic interaction between graphene and encapsulated transition metals that can lead to desired catalytic activities falls likely also into this definition of EAMSI. The general nature of EAMSI is demonstrated below by illustrating more examples of tunability of probe molecule adsorption energies on TM-doped monolayers when these are chemisorbed on a Ni(111) support.

Example 2

A microkinetic model for the MTM reaction was developed to better understand the reaction kinetics of the GR-Rh/Ni(111) catalyst. At 473 K, the turnover frequency (based on $O_2$ consumption) for Rh-hBN/Ni(111) was calculated to be 0.017/s. The apparent activation energy for the catalyst was found to be 0.59 eV. A reaction order of 1 and 0.54 was obtained for $CH_4$(1-50 bar) and $O_2$ (1-5 bar). The rate controlling step (first $CH_4$C—H cleavage) was identified using Campbell's degree of rate control (DRC) and thermodynamic rate control (TRC) analysis.

An important concern regarding methane partial oxidation is the selectivity to methanol since the C—H bond energy of methanol is 0.49 eV lower than that of methane and hence, overoxidation of methanol is possible. Conventional scaling relationships, correlating the activation energies of C—H dissociation and H adsorption energies, suggest that the energy barrier of the methane C—H bond is ~0.55 eV higher than that of methanol. To circumvent the undesired overoxidation of methanol, it has been proposed to mix an adsorbent with strong adsorption energy for methanol with the catalyst to effectively reduce the partial pressure of methanol.

Figure 8:
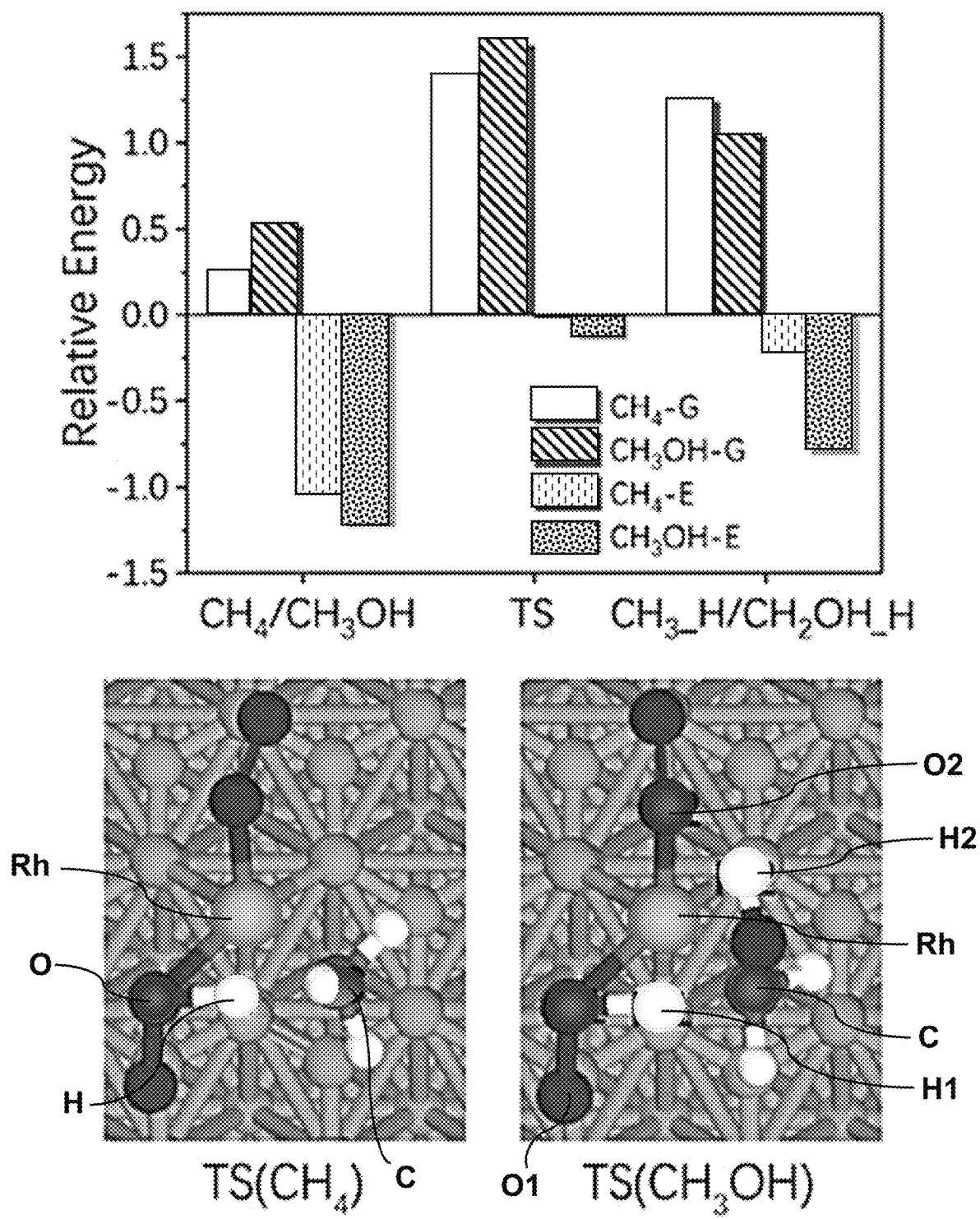
FIG. 8 provides density functional theory (DFT) energy and free energy (T=473 K, $P_{O2}$=1 bar, $P_{CH4}$=50 bar, $P_{CH3OH}$=1 bar) profile for $CH_4$ and $CH_3OH$ C—H breaking by the first surface oxygen on Rh-GR/Ni(111). G denotes free energy and E denote DFT energy. The reference states are set to be the IS in FIG. 6 and FIG. 7 and the corresponding gas molecules.
Figure 9:
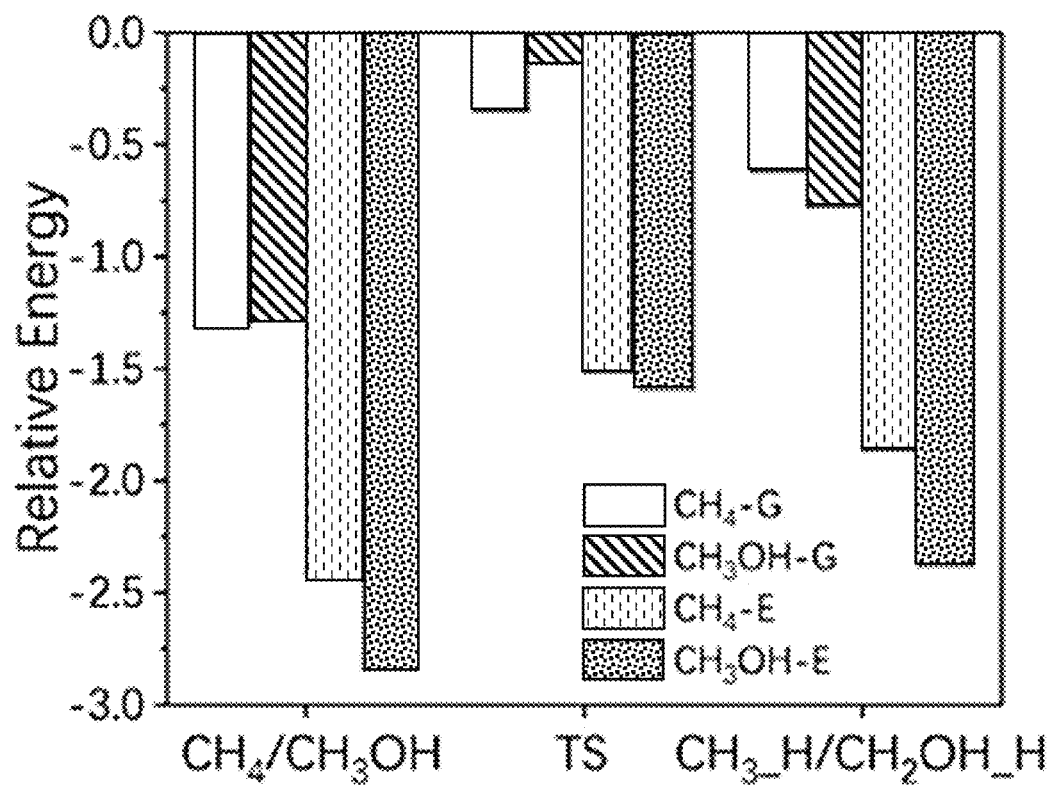
FIG. 9 provides DFT energy and free energy (T=473 K, $P_{O2}$=1 bar, $P_{CH4}$=50 bar, $P_{CH3OH}$=1 bar) profile for $CH_4$ and $CH_3OH$ C—H breaking by the second surface oxygen on Rh-GR/Ni(111). G denotes free energy and E denote DFT energy. The reference states are set to be the IS in FIG. 6 and FIG. 7 and the corresponding gas molecules.
Figure 9:
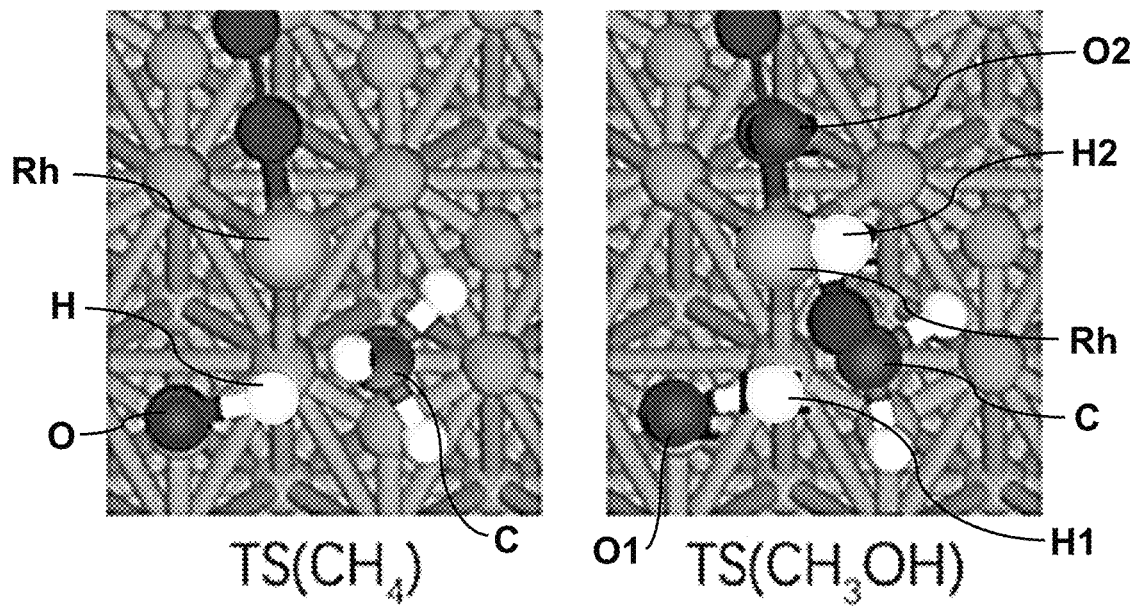

With the present materials, it has been found that the transition state DFT energies for the first and second states in $CH_3OH$. $CH_4$C—H breaking is preferred by ~0.04 eV over that of $CH_3OH$, even when the two molecules have the same partial pressure. As such, overoxidation of methanol can be avoided at significant methane conversion. To understand the unusual selectivity towards methane C—H activation, the spin density of each transition state structure was plotted and it was found that no spin density is localized at the carbon atom. Therefore, these transition state structures are not radicals, different to what is assumed in the well-accepted C—H activation scaling relationship. The bond lengths and Bader charges of the transition state structures were also analyzed (Table 1). In contrast to the conventional radical-like transition state where the $CH_3$-group (or $CH_2OH$-group for the transition state of $CH_3OH$) is only tethered to one surface oxygen atom, the $CH_3$ ($CH_2OH$) of the transition states of the disclosed materials and methods are stabilized by both the surface oxygen and the neighboring Rh with the Rh—C distance being-2.4 Å. As revealed by Bader analysis, both C—H dissociation transition state structures for $CH_3OH$ have a slightly positively charged carbon atom due to the neighboring OH group. In contrast, both C—H dissociation transition state structures for $CH_4$ have a negatively charged carbon atom of about $-0.5 |e^-|$ since carbon is more electronegative than hydrogen. The repulsive electrostatic C—Rh interactions for the $CH_3OH$ transition state and attractive C—Rh interactions for the $CH_4$ transition state lead to a significantly narrowed energy difference between the $CH_3OH$ and $CH_4$ transition states. This observation is also consistent with the shorter C—Rh distance for the two $CH_4$ transition state structures. It was noted that the $O_2$—$H_2$ bond distances (FIG. 8, FIG. 9) for both $CH_3OH$ transition state structures are ~2 Å such that also the hydrogen bond stabilization in the $CH_3OH$ transition state structures is very weak. Overall, the synergy of the oxygen and the neighboring cationic Rh leads to the stabilization (destabilization) of the transition state for $CH_4$ ($CH_3OH$).

Table 1, below, provides bond lengths and Bader charges of transition state (TS)($CH_4$) and transition state (TS) ($CH_3OH$) on the first and second surface oxygen on GR-Rh/Ni(111). Atoms are labeled identically to those in FIG. 8 and FIG. 9.

TABLE 1

| | | First oxygen | | | Second oxygen | | |
|---|---|---|---|---|---|---|---|
| | | TS($CH_4$) | | TS($CH_3OH$) | | TS($CH_4$) | TS($CH_3OH$) |
| Bond Length (Å) | O—H | 1.185 | O1—H1 | 1.204 | O—H | 1.208 | O1—H1 1.246 |
| | C—H | 1.498 | C—H | 1.476 | C—H | 1.478 | C—H 1.443 |
| | Rh—C | 2.340 | Rh—C | 2.418 | Rh—C | 2.346 | Rh—C 2.423 |
| | | | O2—H2 | 2.001 | | | O2—H2 1.979 |
| BaderCharge ($|e-|$) | Rh | 0.76 | Rh | 0.75 | Rh | 0.70 | Rh 0.67 |
| | C | −0.50 | C | 0.17 | C | −0.52 | C 0.15 |
| | | | O2 | −0.29 | | | O2 −0.28 |
| | | | H2 | 0.74 | | | H2 0.67 |

$CH_4$C—H cleavage is only 0.13 and 0.08 eV higher than that of $CH_3OH$ occurring at the same adsorption site, respectively, breaking the scaling relationships of the transition state energies for methane and methanol C—H bond activation. Under reaction conditions of a $CH_4$ partial pressure of 50 bars and a $CH_3OH$ partial pressure of 1 bar, the free energies of the C—H bond cleavage transition states in $CH_4$ for the first and second surface oxygen are 0.19 and 0.22 eV lower than those for the C—H bond cleavage transition Example 3

Figure 10:
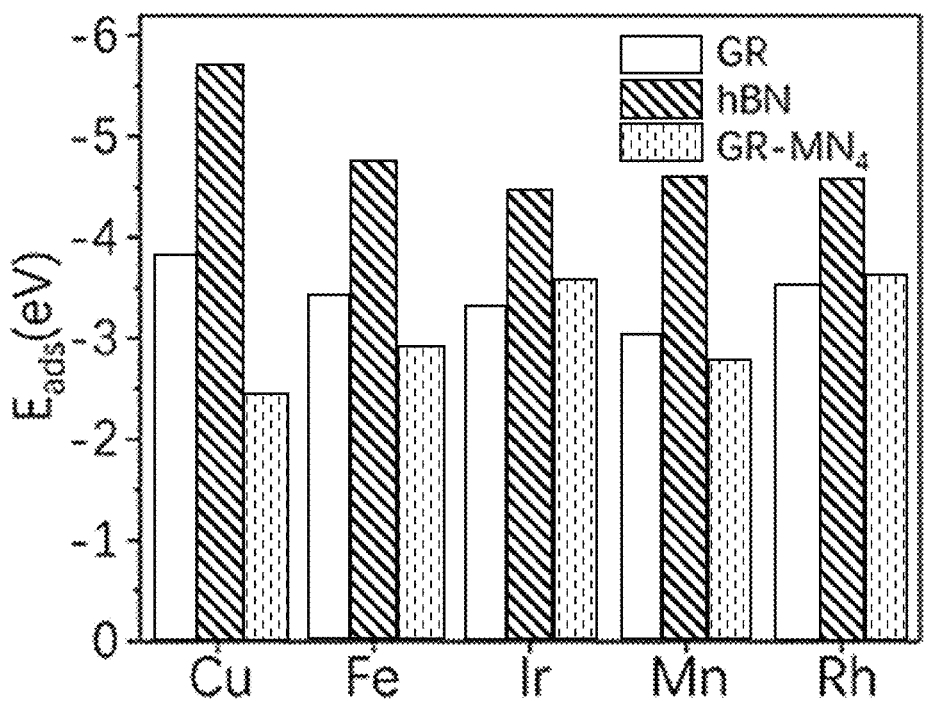
FIG. 10 presents adsorption energies of Cu-, Fe-, Ir-, Mn-, and Rh-doped graphene (GR), hexagonal boron nitride (hBN) and N-doped graphene featuring $MN_4$(GR-$MN_4$) on (4×4) Ni(111).
Figure 13:
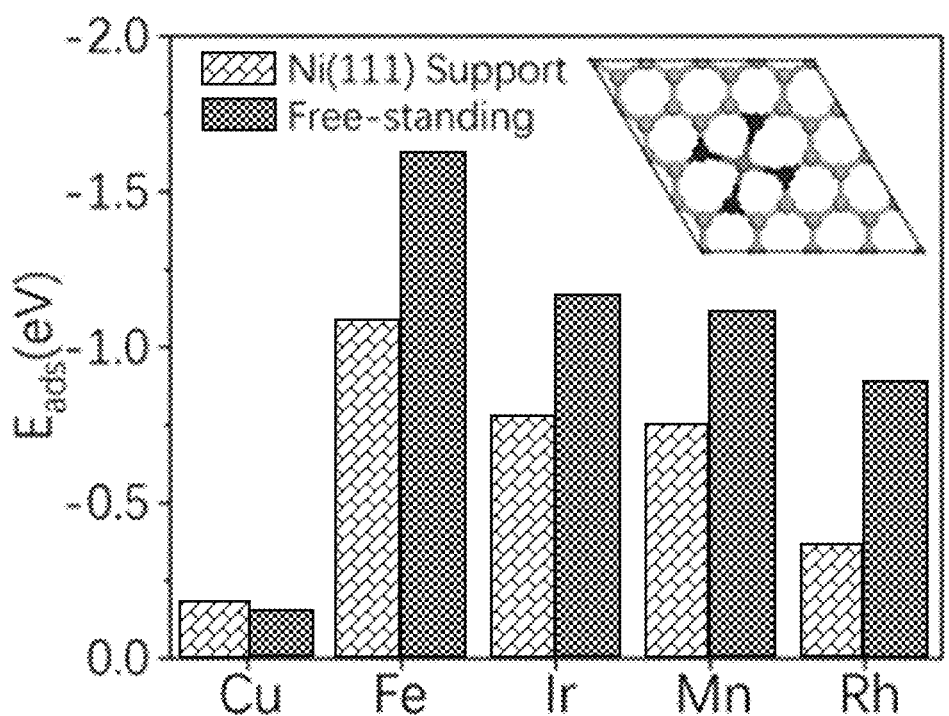
FIG. 13 presents adsorption energies of CO on $Mn_4$-embedded graphene. The insets in FIG. 13 displays the configuration of $RhN_4$-graphene.

The universality of changing the adsorption strength of various molecules on TM-doped 2D materials by chemisorption on Ni(111) was explored. Cu, Fe, Ir, Mn, and Rh are common active elements in heterogeneous catalysis and were therefore tested for doping graphene, hBN, and N-doped graphene featuring a MN4 motif (FIG. 13). The study of TM-atoms immobilized in N-doped graphene featuring a MN4 motif is a recently emerging topic in single-atom electrocatalysis. FIG. 10 provides the adsorption energies of these TM-doped monolayers on Ni(111).

Figure 11:
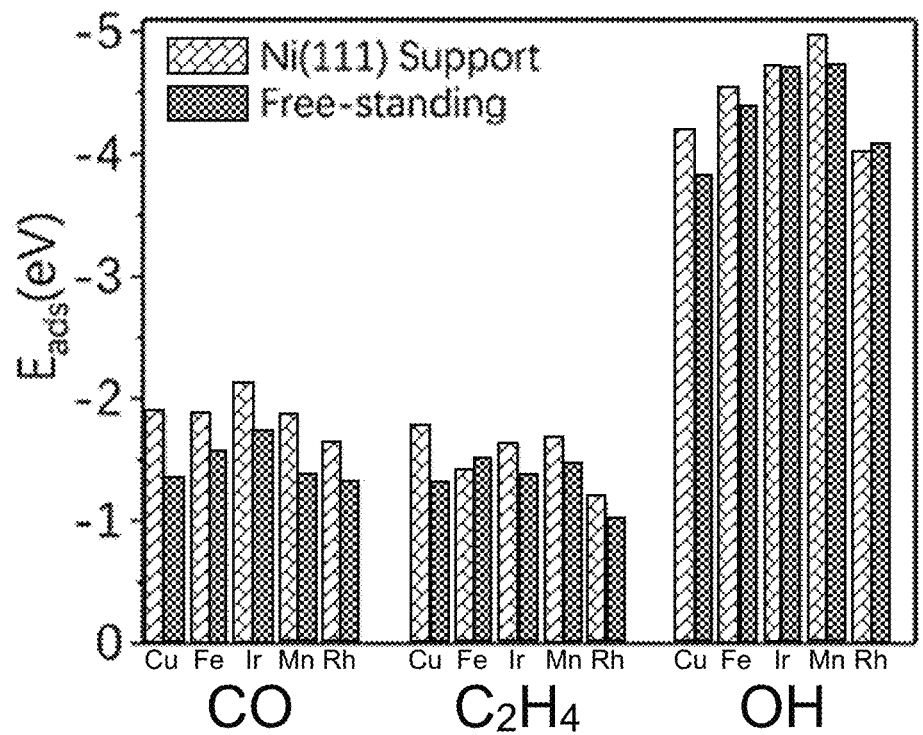
FIG. 11 presents adsorption energies of CO, $C_2H_4$, and OH on Ni(111) supported Cu, Fe, Ir, Mn and Rh-doped GR as well as free-standing samples.

The adsorption strength of CO, $C_2H_4$, and OH were examined for TM-doped GR. FIG. 11 presents the results. In general, the presence of the Ni(111) support had a noticeable effect on the adsorption energy. For example, the $E_{ads}$ of CO on GR-Cu/Ni(111) and GR-Cu were −1.87 and −1.34 eV, respectively. Also, the $E_{ads}$ of $C_2H_4$ on GR-Ir/Ni(111) was −1.62 eV compared with −1.36 eV on GR-Ir.

Figure 12:
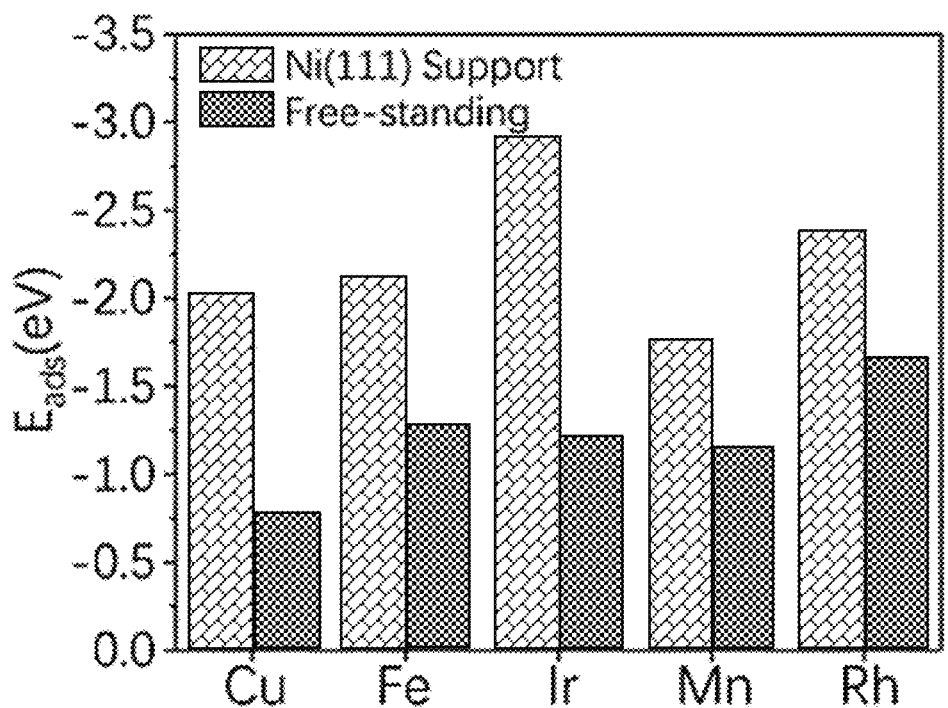
FIG. 12 presents adsorption energies of CO on transition metal (TM)-doped hBN including Cu-, Fe-, Ir-, Mn-, and Rh-doped hBN.

The adsorption of CO was also used to probe the properties of Ni(111)-supported and free-standing TM-doped hBN (FIG. 12) and graphene-MN4 (FIG. 13).

The adsorption energy of a molecule can also be tuned by doping Ni(111) with a heteroatom. When a Ni atom underneath a dopant-bonded N in hBN is replaced with Cu, the $E_{ads}$ for CO on hBN-Cu/Ni(111) was −1.82 eV, as compared with the pristine Ni(111) case of −2.00 eV.

Example 4

Figure 14:
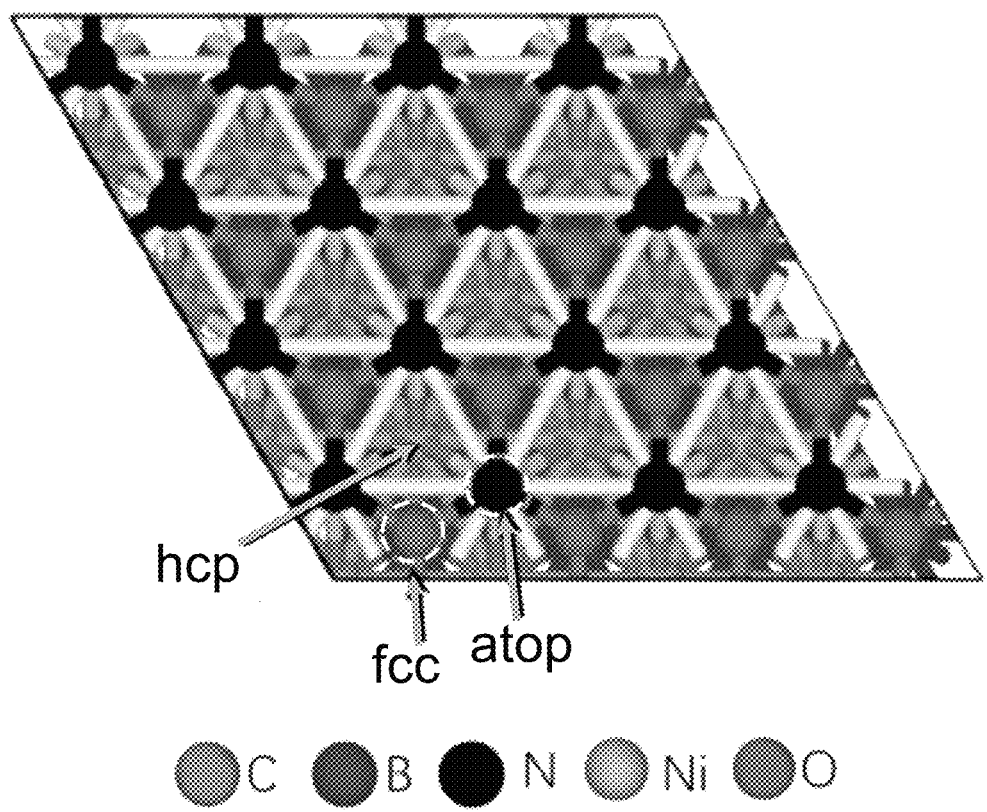
FIG. 14 schematically illustrates an adsorption configuration of hBN on a five-layer (4×4) Ni(111) support. The element identification of FIG. 14 holds for all of FIG. 14 through FIG. 18.
Figure 15:
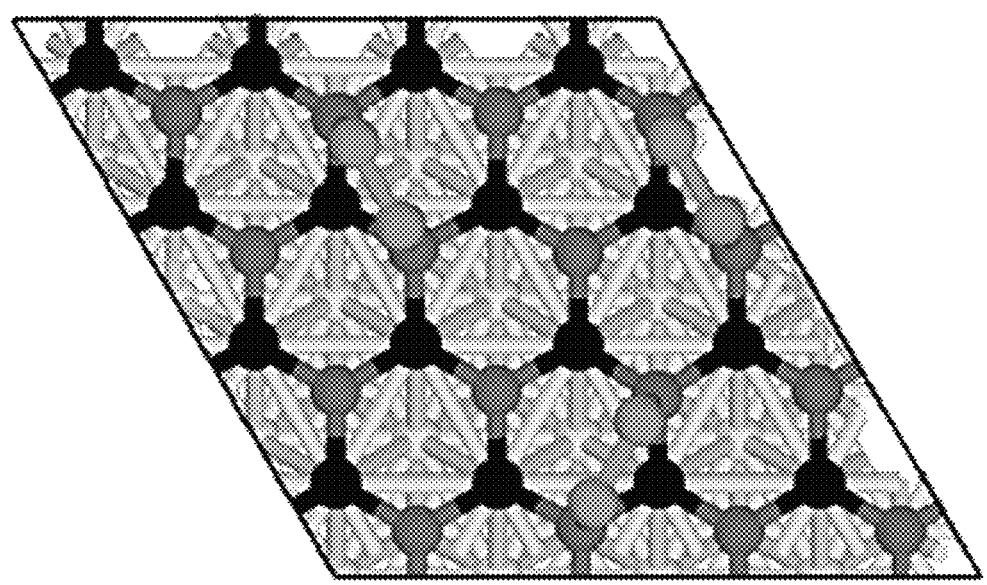
FIG. 15 schematically illustrates adsorption of three $O_2$ molecules on hBN/Ni(111).
Figure 16:
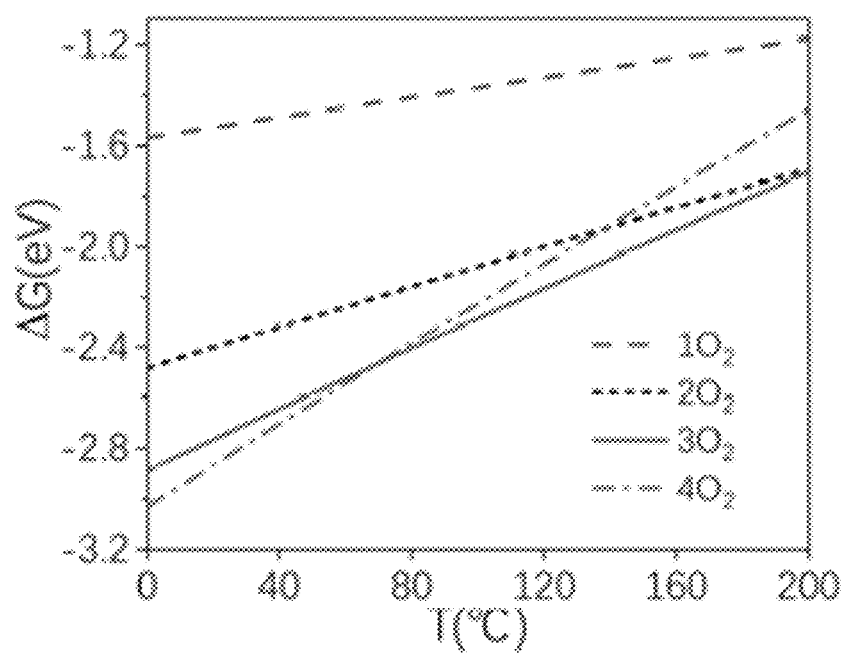
FIG. 16 presents Gibbs free energies of $O_2$ adsorption on hBN/Ni(111) at various coverages, the $O_2$ partial pressure is set to 0.01 bar.

Identification of PROX catalysts was carried out starting from hBN/Ni(111) (FIG. 14) in which boron is situated at the hcp site and nitrogen is situated at the atop site. The chemisorption energy of hBN on the (4×4) Ni(111) was calculated to be −3.93 eV. $O_2$ molecules were found to be chemisorbed strongly on hBN/Ni(111) with the neighboring boron atoms occupied by two oxygen atoms (FIG. 15), which contrasts the case of free-standing hBN where $O_2$ is only physiosorbed. Bader charge analysis suggests that a (4×4) hBN layer has a total negative charge of −1.13 |e⁻|, indicative of the formation of chemical bonds between hBN and Ni(111). Upon the chemisorption of $O_2$, Ni(111) can serve as an electron reservoir and compensate the loss of electrons transferred from hBN to $O_2$. Each chemisorbed $O_2$ has a negative charge of about −1.8 |e⁻| and the O—O bond length is elongated to a range of 1.46 to 1.50 Å, depending on the number of $O_2$ molecules on hBN/Ni(111). Therefore, the presence of a Ni(111) support leads to a significant modification of the properties of hBN. Constrained thermodynamics calculations suggest that up to three $O_2$ molecules can be accommodated on a (4×4) hBN/Ni(111) at 80° C. and at a $O_2$ partial pressure of 0.01 bar (FIG. 16), following typical operation conditions of the PROX reaction.

The oxidation of CO on hBN/Ni(111) loaded with three $O_2$ molecules was investigated. However, a free energy barrier of 1.19 eV (80° C., CO partial pressure is 0.01 bar) was observed, corresponding to a forward rate constant of only 7.89×10⁻⁵/s, suggesting that hBN/Ni(111) is not a good candidate for catalyzing CO oxidation under PROX reaction conditions.

Figure 17:
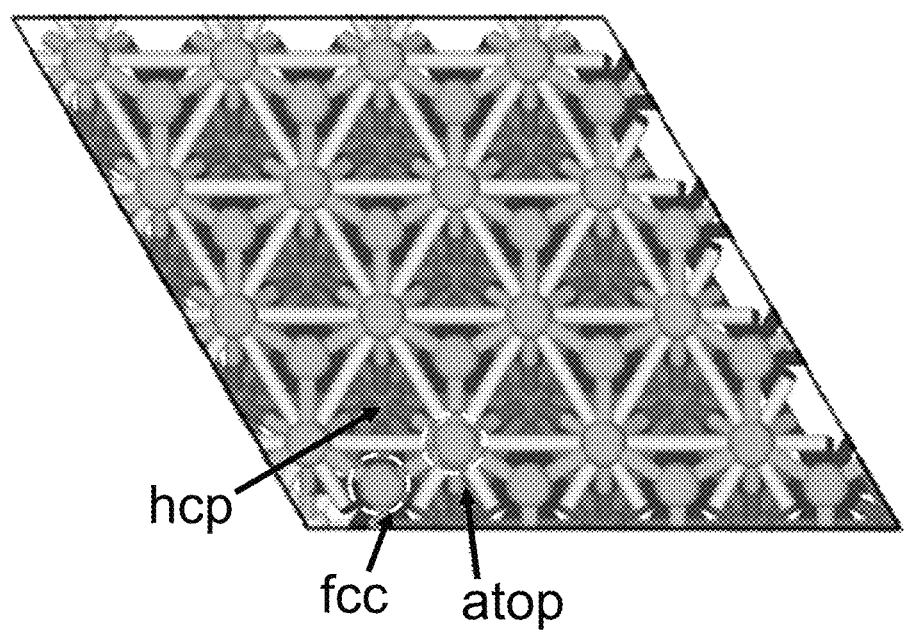
FIG. 17 schematically illustrates adsorption of GR on a 4×4 Ni(111) support.

The case of Ni(111)-supported graphene was also considered. Calculations suggested that GR is preferably adsorbed on Ni(111) with an atop/fcc configuration (FIG. 17). The adsorption energy was calculated to be −2.10 eV for a (4×4) graphene layer. In the case of hBN/Ni(111), $O_2$ can be adsorbed strongly on a boron site, and it was speculated that the presence of a boron dopant in GR/Ni(111) can lead to the chemisorption of $O_2$. It was noted that boron-doped graphene (B-GR) has been synthesized and used as electrocatalysts. A carbon atom on top of the Ni fcc site was replaced with a boron atom to construct the atomistic model shown in FIG. 17, which is the most favorable adsorption configuration and the adsorption energy of B-GR on Ni(111) was calculated to be −4.03 eV. A Bader charge calculation suggests that B-GR gains 1.39 e⁻ from Ni(111).

Figure 18:
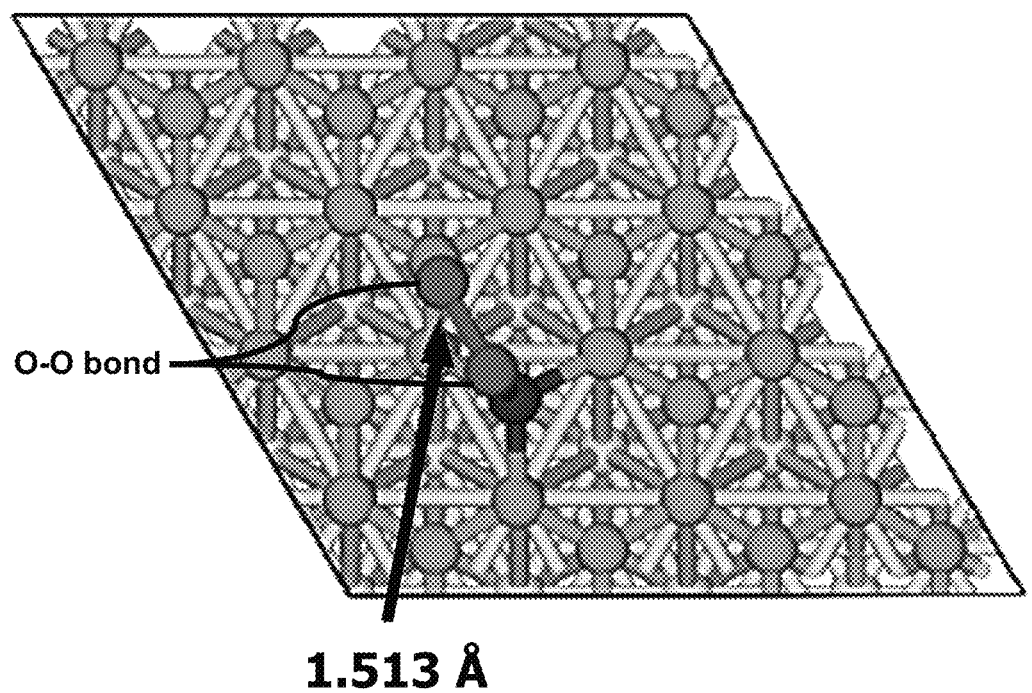
FIG. 18 schematically illustrates adsorption of one $O_2$ molecule on boron doped (B)-GR/Ni(111).

The O—O bond is elongated to 1.513 Å upon adsorption on B-GR/Ni(111) (FIG. 18). As illustrated, one oxygen binds to a fcc carbon while the other one binds to boron. The chemisorption of $O_2$ on B-GR/Ni(111) contrasts that on free-standing B-GR where $O_2$ is only physiosorbed. Apart from $O_2$, all other investigated molecules in the present study (including CO) were physiosorbed on B-GR/Ni(111).

Figure 19:
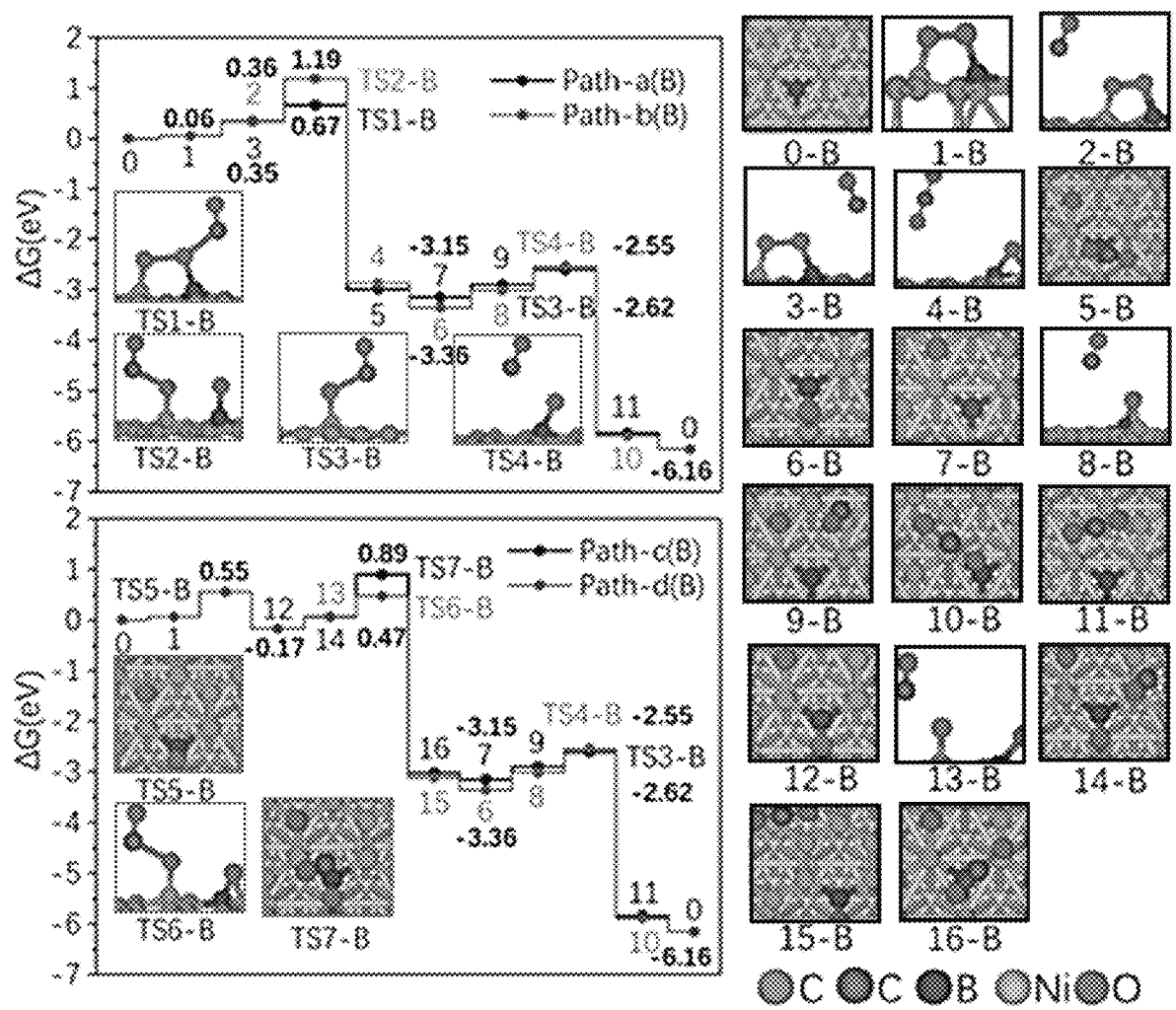
FIG. 19 presents free energy profiles of CO oxidation on B-GR/Ni(111) at 353K.

FIG. 19 illustrates the free energy diagram of CO oxidation on B-GR/Ni(111) calculated at 353K. The partial pressures of all gas phase molecules were set to be 1 bar. In Path-a(B) and b(B), CO reacts with oxygen before $O_2$ dissociation occurs; in Path-c(B) and d(B), CO reacts with atomic O. Boron doping is denoted as B in each intermediate and transition state. The B in each intermediate state along the energy profile is omitted for clarity.

CO can react with the pristine $O_2$ on B-GR/Ni(111) (see FIG. 19, Path-a(B) and b(B)) or atomic O after the dissociation of the O—O bond (Path-c(B) and d(B)). The adsorption of $O_2$ is only slightly endergonic by 0.06 eV. In Path-a(B), CO reacts with the O adsorbed at the boron site first, which is concomitant with the dissociation of the O—O bond and has an effective barrier of 0.67 eV (3-B→5-B). 5-B→7-B and 4-B→6-B correspond to the desorption of $CO_2$. The second CO reacts with the O adsorbed on the C site and the effective barrier amounts to 0.53 eV (9-B→11-B). In Path-b(B), CO reacts first with the 0 adsorbed at the carbon site. The effective barriers for CO oxidation along Path-b(B) are 1.19 and 0.81 eV, respectively.

The dissociation of the O—O bond has an effective barrier of 0.55 eV, whose free energy of reaction is exergonic by −0.17 eV (1-B→12-B). After O—O bond dissociation, one oxygen atom binds to one carbon atom in an upright configuration while the other oxygen is shared by a boron and a carbon atom (12-B, called B-bonded oxygen hereafter). The comparatively weak adsorption of oxygen on B-GR/Ni(111) is beneficial for the removal of oxygen by CO. The reaction of the C-bonded 0 with the first CO (13-B→15-B) has an effective barrier of 0.64 eV (Path-d(B)) while the reaction for the B-bonded O (14-B→16-B) has a barrier of 1.06 eV (Path-c(B)). The remaining parts of Path-c(B) and d(B) are identical with those of Path-a(B) and b(B), respectively. Since an oxygen atom can migrate from a boron site to a carbon site (6-B→7-B) by overcoming a barrier of 0.84 eV (Table 51), the second CO oxidation can also occur through the pathway 6-B→7-B→9-B→11-B. Throughout the process, an Eley-Rideal mechanism of CO oxidation is followed. Considering the energy profiles of Path-a, b, c and d(B), we can deduce that the first CO oxidation mainly proceeds through the path 12-B→→13-B→15-B. For the second CO oxidation, if the effective barrier of 6-B→TS4-B→10-B (possible when the CO partial pressure is noticeable lower than 1 bar) is higher than that of the oxygen migration (6-B→7-B), then a 6-B→7-B→9-B→11-B pathway is followed, which lowers the effective barrier by 0.07 eV relative to the pathway though TS4-B. In other words, the oxygen migration from the boron site to the carbon site can possibly lower the effective barrier of the second CO oxidation at lower partial pressures of CO due to the fact that TS3-B is 0.07 eV lower than TS4-B.

For the reaction of $H_2$ with $O_2$ adsorbed on B-GR/Ni(111), an elementary reaction step involving the dissociation of $O_2$ and formation of $H_2O$ was not found, i.e., $O_2$ dissociation has to occur prior to the reaction of atomic O with $H_2$. Since the $H_2$ molecule is only weakly physiosorbed on B-GR/Ni (111), an Eley-Rideal mechanism was again followed (the partial pressures of all gas phase molecules are set to be 1 bar).

Figure 20:
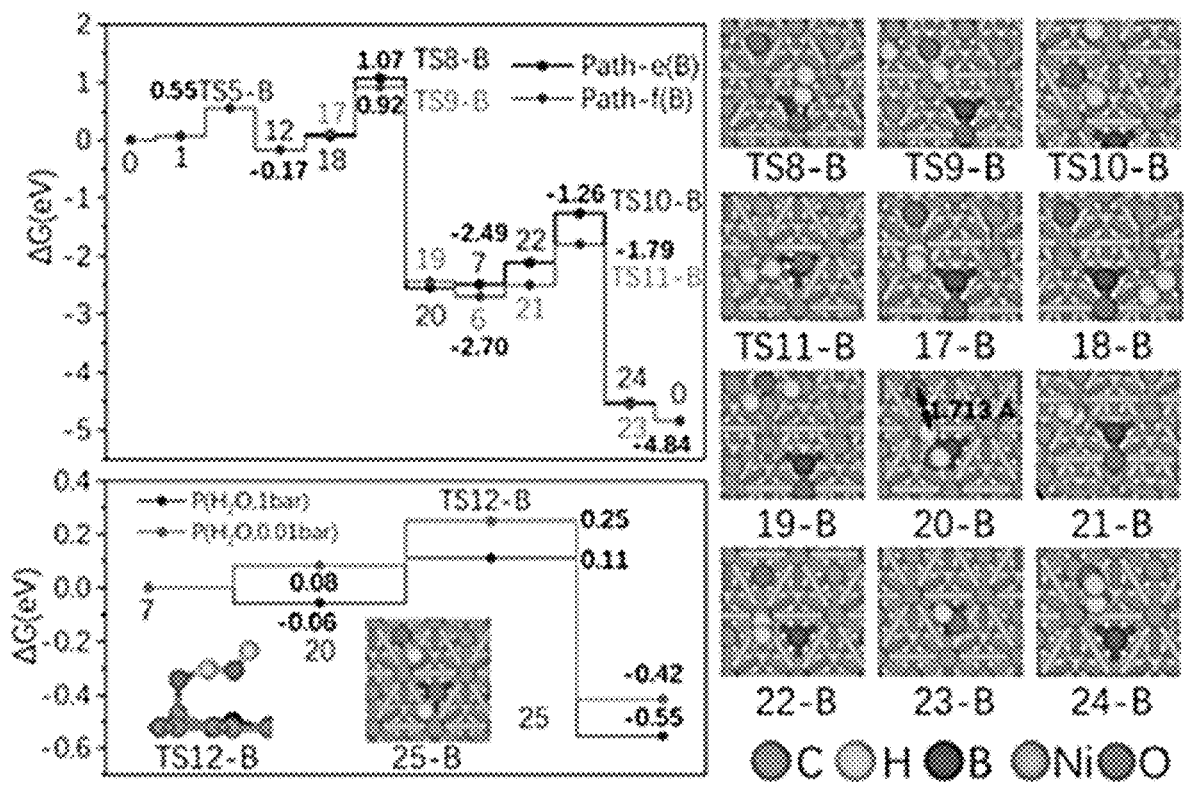
FIG. 20 presents free energy profiles of $H_2$ oxidation (above) as well as the formation of two hydroxyls by an oxygen atom and water (below) on B-GR/Ni(111) at 353K.

FIG. 20 illustrates that the reaction of the first $H_2$ with the O at the boron site has an effective barrier of 1.24 eV (18-B→20-B, Path-e(B)), as compared with the O on the carbon site which has a barrier of 1.09 eV (17-B→19-B, Path-f(B)). Along Path-e(B), the reaction of the second $H_2$ and the C-bonded O (7-B→24-B) has an effective barrier of 1.23 eV, while the reaction of the second atomic O (6-B→23-B) along Path-f(B) has a lower barrier of 0.91 eV. The reactions of $H_2$ with boron-bonded oxygen feature early transition states (TS7-B and TS10-B, see TS configurations in FIG. 20) while those involving carbon-bonded oxygen feature late transition states (TS8-B and TS9-B). For the reaction of each oxygen atom, it was observed that CO had a higher reactivity than $H_2$, which is due to the fact that the formation of $H_2O$ requires the insertion of the oxygen atom into the H—H bond of the physiosorbed $H_2$, while $CO_2$ is formed simply by the approach of CO to the adsorbed oxygen. Moreover, the dissociation of $H_2$ on B-GR/Ni(111) was examined in the absence of adsorbed oxygen, which has a high barrier of 2.40 eV and is endergonic by 1.12 eV. From the above, it was obvious that an oxygen atom bonded to a boron and a carbon have distinct reactivities. This can be traced back to the different adsorption configurations of oxygen in 6-B and 7-B, where an oxygen atom binds to both boron and carbon atoms in the case of 6-B, and only to a carbon atom in the latter case of 7-B (see FIG. 19).

Under PROX reaction conditions, the presence of water is unavoidable. Therefore, the presence of water was incorporated in the reaction pathways on B-GR/Ni(111). 20-B→25-B corresponds to the reaction of an adsorbed water and an oxygen atom, which produces two hydroxyl groups and has a low barrier of 0.17 eV at a water pressure of 1 bar (see FIG. 20). At a water partial pressure of 0.01 bar, which is more typical for PROX reactors, the energy profile shown in FIG. 20 suggests that 25-B is 0.42 eV lower than 7-B. The reaction of 25-B and a physiosorbed CO may proceed through a COOH mechanism of CO oxidation, which is common for chemisorbed CO and OH that can produce a COOH intermediate, followed by cleavage of the O—H bond to produce $CO_2$. However, a COOH mechanism was not identified, likely because the approach of the CO to the B-GR/Ni(111) surface is energetically unfavorable. To react with CO, the two hydroxyl groups need to form an adsorb oxygen and a water molecule (25-B→20-B), followed by facile water desorption (25-B→7-B). Considering that the effective barrier of 6-B→TS4-B→10-B at a CO partial pressure of 0.01 bar (PROX condition) is calculated to be 0.95 eV (i.e., it is higher than the oxygen migration barrier of 0.84 eV, see Table S1), the second CO oxidation preferably proceeds through 6-B→7-B→9-B→11-B with an effective barrier of 0.88 eV. However, in the presence of $H_2O$ (0.01 bar), the effective barrier of the second CO oxidation on B-GR/Ni(111) is increased by 0.42 eV, being 1.30 eV, which is translated to a low forward reaction rate of $2.03\times 10^{-6}$/s. Thus, it was concluded that CO oxidation on B-GR/Ni(111) was poisoned by water dissociation under PROX reaction condition.

Figure 21:
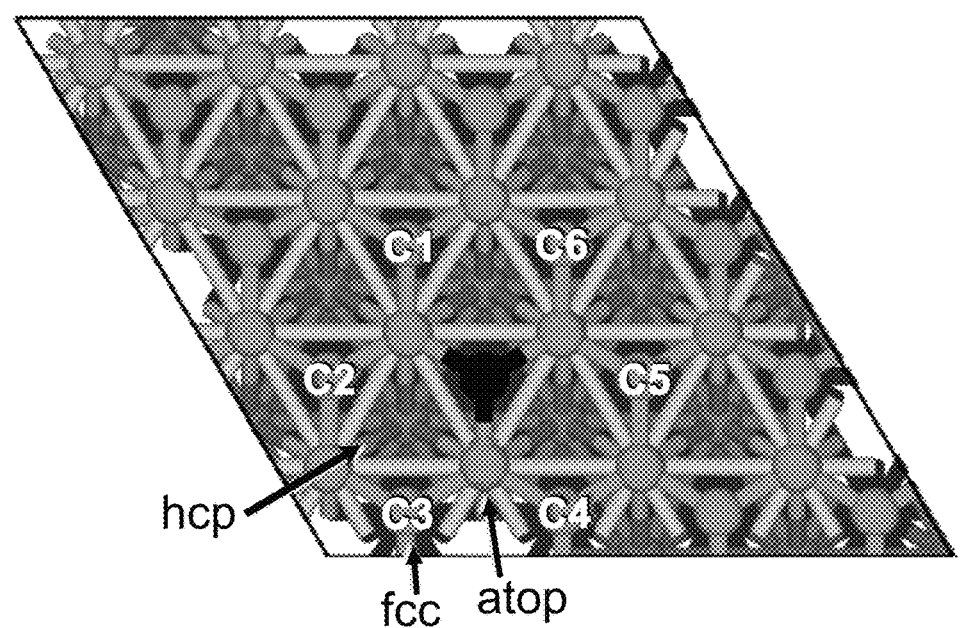
FIG. 21 illustrates adsorption configuration of nitrogen (N)-doped GR on a five-layer (4×4) Ni(111) support. (C1-C6 are equivalent carbon atoms.)
Figure 22:
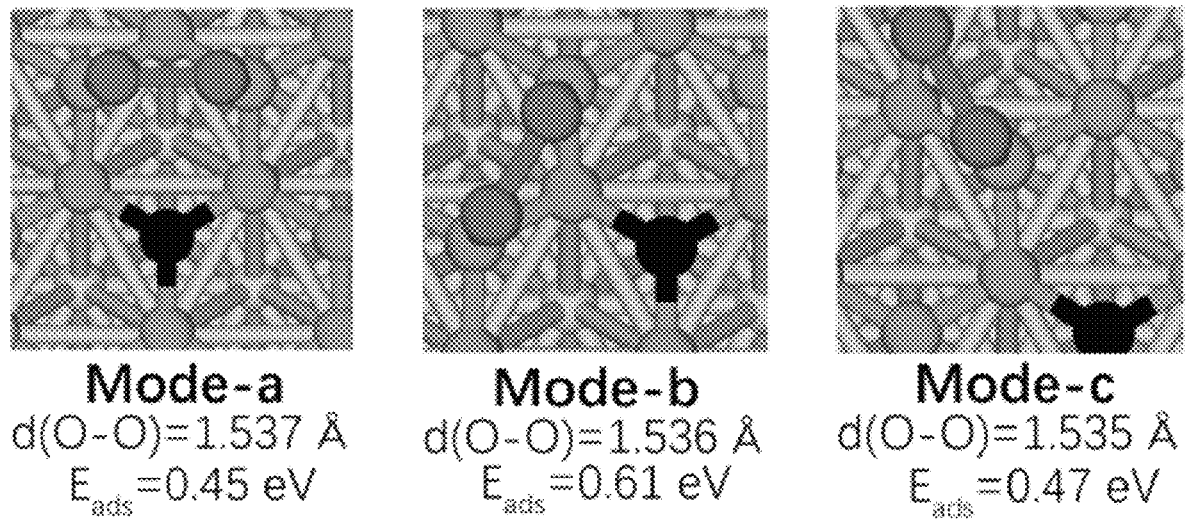
FIG. 22 illustrates different chemisorption configurations of $O_2$ on N-GR/Ni(111).

As B-GR/Ni(111) appeared to be not a good active site model for a PROX catalyst, the PROX reaction on nitrogen-doped graphene supported on Ni(111) was examined. Various reaction pathways involving the dissociation of water were considered, and the most favorable adsorption configuration of N-GR on Ni(111) were identified (FIG. 21), whose adsorption energy is −2.35 eV. Bader charge calculations suggest that the N-GR unit cell gains 1.58 $e^-$ from Ni(111). It was found that an $O_2$ molecule can be chemisorbed on N-GR/Ni(111) in three different configurations (Mode-a, b and c in FIG. 22). In all cases, one or two next nearest carbon atoms of the nitrogen site (C1-C6 in FIG. 21) are occupied by oxygen. Other chemisorption configurations of $O_2$ for which other carbon atoms or the nitrogen site are adsorption sites of oxygen were not identified.

Figure 23:
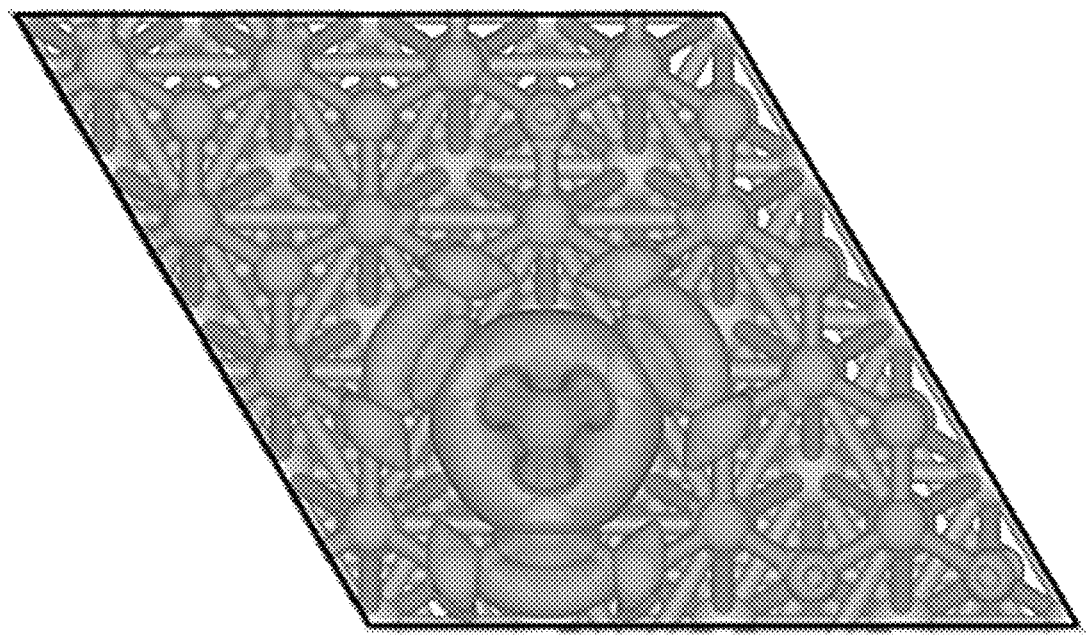
FIG. 23 presents charge density difference upon the deposition of Non Ni(111)-supported graphene with a carbon defect.

A charge density difference plot in which the accumulation (depletion) of electrons is denoted by yellow (blue) is presented in FIG. 23. The isosurface value is 0.003|e-|/Å3. The plot suggested that upon the deposition of nitrogen at the carbon defect site of GR/Ni(111), the charge surrounding the nitrogen atom redistributes and charge accumulation occurs on the six next nearest carbon atoms, C1-C6, which is believed to be the reason for the favorable $O_2$ chemisorption on N-GR/Ni(111). In the case of free-standing N-GR, $O_2$ is only physisorbed.

Figure 24:
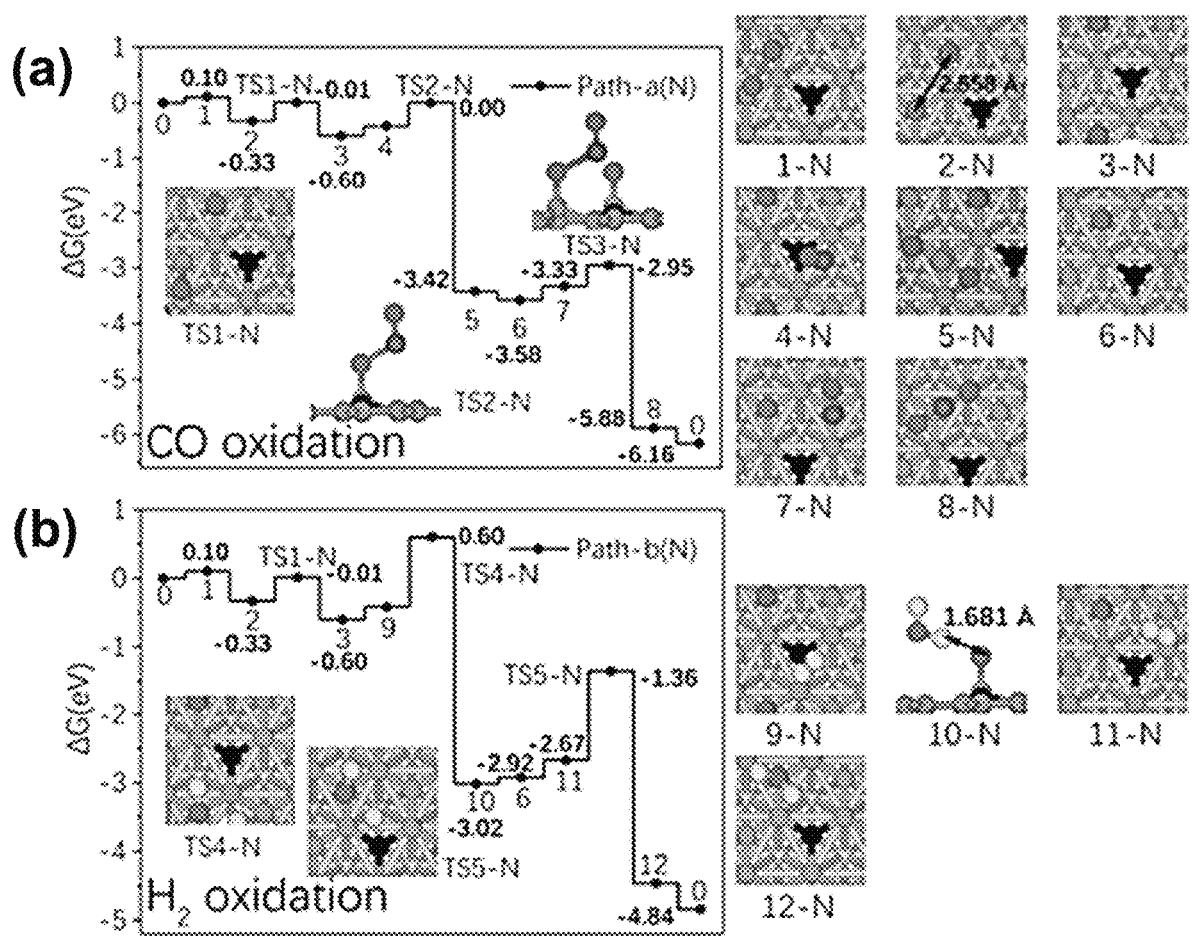
FIG. 24 presents free energy profiles of CO (a) and $H_2$ oxidation (b) on N-GR/Ni(111) at 353K without the dissociation of $H_2O$.

The energy profiles (Path-a(N) and b(N)) of CO and $H_2$ oxidation were examined for the most favorable $O_2$ adsorption configuration Mode-b, as displayed in FIG. 24 (the partial pressures of all gas phase molecules are set to be 1 bar). $O_2$ adsorption is slightly endergonic at 353K (1-N), followed by O—O dissociation which involves a vanishingly small barrier. Compared with the O—O bond dissociation on B-GR/Ni(111), the more favorable O—O dissociation on N-GR/Ni(111) can be attributed to the fact that an upright adsorption configuration of oxygen on boron in TS5-B is unfavorable for the B-GR/Ni(111). The two oxygen atoms of 2-N have a comparatively short distance of 2.558 Å, the migration of one oxygen to another carbon site leads to a decrease in free energy of 0.27 eV, which was attributed to a decrease in electrostatic repulsion between the negatively charged oxygen atoms. The physiosorbed CO can react with oxygen atoms adsorbed on N-GR/Ni(111) through the path 3-N→4-N→5-N and 6-N→7-N→8-N, the effective barrier of which was calculated to be 0.60 eV and 0.57 eV at 353K respectively. The $H_2$ oxidation possesses a significantly higher activation barrier than the CO counterpart, being 1.20 eV for 3-N→9-N→10-N and 1.56 eV 6-N→11-N→12-N, respectively. Note that the desorption of $H_2O$ (10-N→9-N) is slightly endergonic at a high $H_2O$ partial pressure of 1 bar due to the relatively strong hydrogen bond between hydrogen and oxygen (denoted 10-N in FIG. 24 at b).

Figure 25:
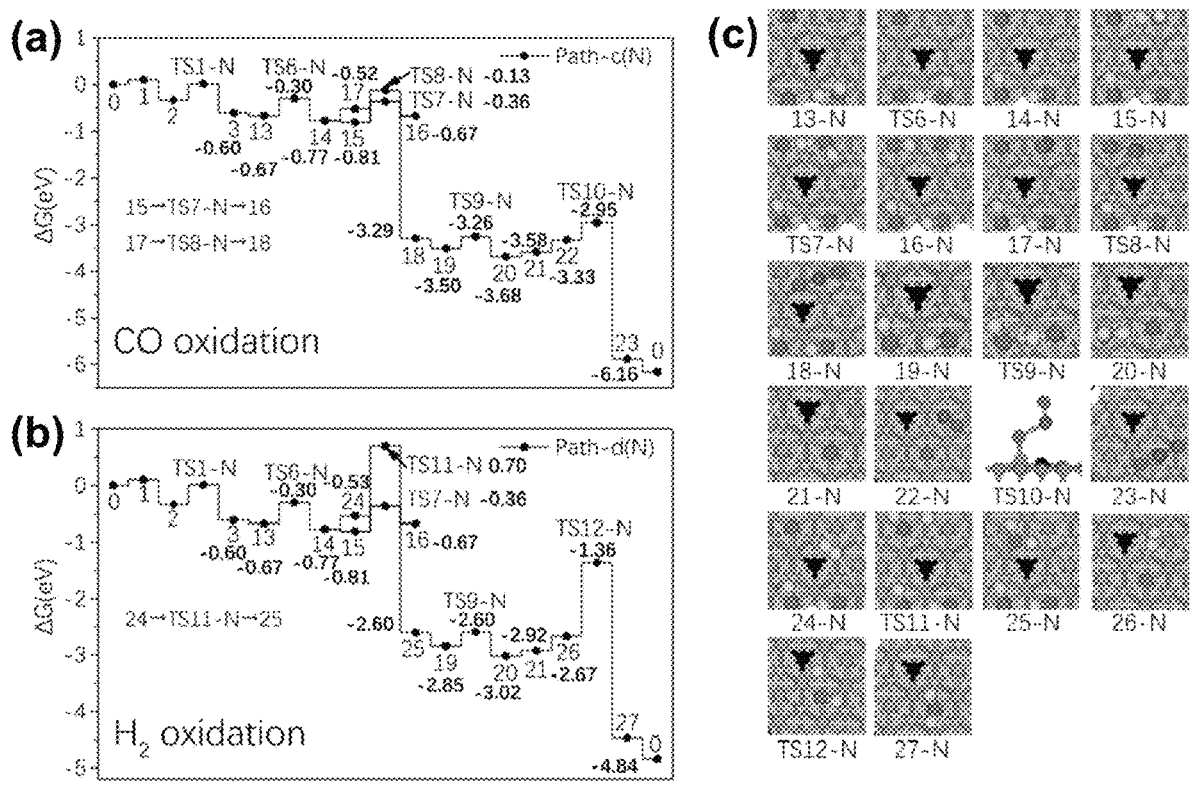
FIG. 25 presents free energy profiles of CO (a) and $H_2$ oxidation (b) on N-GR/Ni(111) at 353K involving the dissociation of $H_2O$. At (c) is shown the configurations of all intermediate and transition states (TS). The partial pressures of all gas phase molecules are set to be 1 bar.

Reaction pathways (Path-c(N) and d(N)) of $H_2$ and CO oxidation on N-GR/Ni(111) involving the dissociation of water were also investigated. Results are shown in FIG. 25. Starting from 3-N, oxygen can react with adsorbed $H_2O$ to form hydroxyl groups. 14-N featuring two hydroxyl groups is 0.17 eV lower in free energy than 3-N, whereas 16-N featuring four hydroxyl groups is 0.10 eV higher in energy than 14-N. Therefore, the formation of hydroxyl groups on N-GR/Ni(111) is less thermodynamically favorable than the 7-B→20-B→25-B counterpart of B-GR/Ni(111). 14-N can react with CO by overcoming an effective barrier of 0.64 eV to form 18-N. Upon the formation of the first $CO_2$, the two hydroxyl groups of 19-N can form an adsorbed oxygen and $H_2O$, which is energetically downhill by 0.18 eV. While the 21-N→22-N→23-N path occurs at a different active site than the 6-N→7-N→8-N path (see FIG. 24 at a and FIG. 25 at a), the energy profiles of the two processes are the same since the oxygen atoms of 21-N and 6-N are equivalent (see above). $H_2$ can also be oxidized on N-GR/Ni(111) in the same vein as CO through 14-N→24-N→25-N and 21-N→26-N→27-N, respectively, with noticeable higher activation energies than the CO oxidation. It is emphasized that the energetically uphill process of 14-N→15-N→16-N and downhill process of 19N→20-N→21-N (even if the $H_2O$ partial pressure is 1 bar) ensure that no hydroxyl group poisoning occurs for the N-GR/Ni(111) catalyst.

Figure 26:
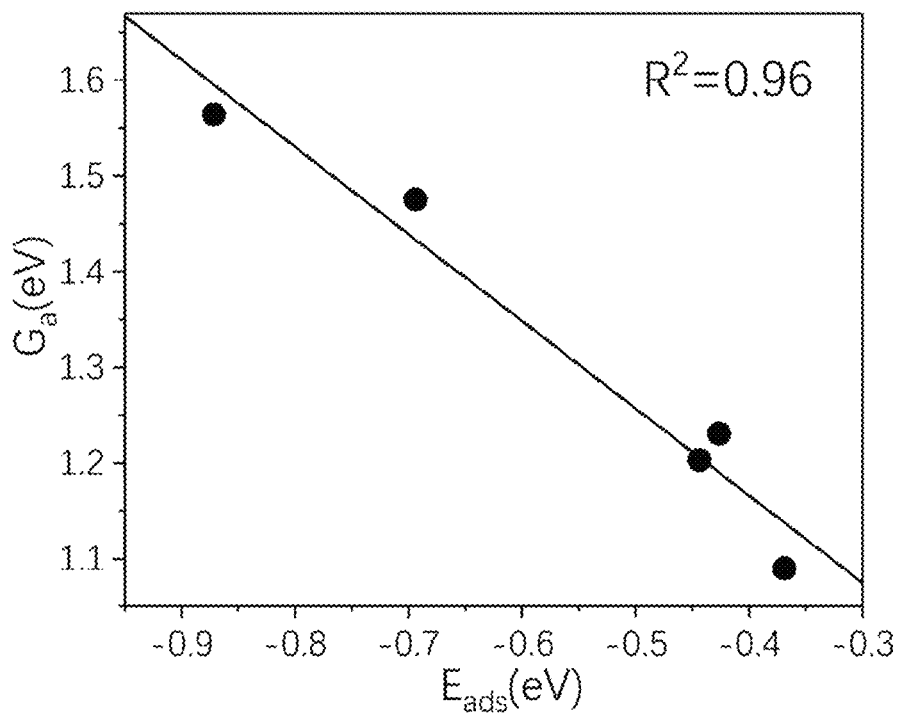
FIG. 26 presents scaling relation between the effective barrier ($G_a$, 353 K, the $H_2$ pressure is 1 bar) of $H_2$ oxidation by O adsorbed at the carbon site on B-GR/Ni(111) and N-GR/Ni(111) versus the O adsorption energy ($E_{ads}$). $G_a$=0.911×$E_{ads}$+0.802. The reference state of $E_{ads}$ is the clean surface and $0.5O_2$ in the vapor phase.

To this end, the energy profiles of the CO and $H_2$ oxidation on B-GR/Ni(111) and N-GR/Ni(111) was examined. It was found that at 353K, CO oxidation by an adsorbed oxygen at a carbon site has an effective barrier of around 0.60 eV, which is not sensitive to the environment of the active sites. In comparison, the effective barrier of $H_2$ oxidation at the carbon site ranged from 1.09 eV (12-N→TS9-N→19-N) to 1.56 eV (6-N→TS5-N→12-N), which can be correlated with the oxygen adsorption energy (see FIG. 26). Hence, a lower oxygen adsorption energy is favorable for the formation of water. It was noted that the scaling relation of $H_2$ oxidation on the C-bonded oxygen is not applicable for the B-bonded oxygen, i.e., the scatter in the data is large, probably due to the different adsorption configuration of the B-bonded oxygen.

Example 5

Figure 27:
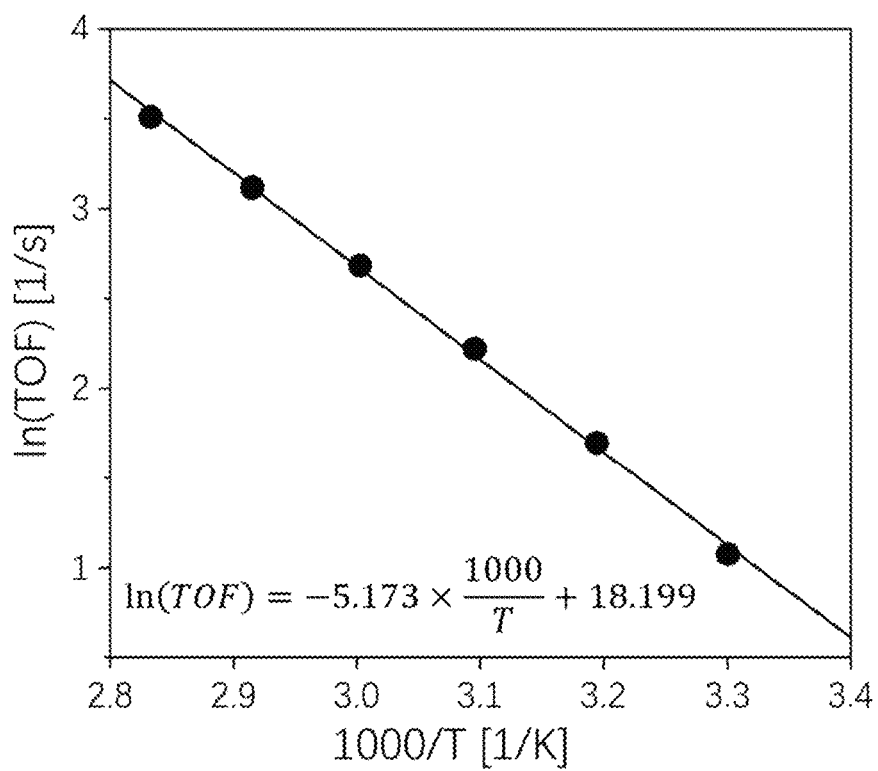
FIG. 27 provides an Arrhenius plot for CO/$H_2$ oxidation, i.e., $O_2$ consumption, over N-GR/Ni(111) in the temperature range 300-353K.

A microkinetic model was developed to understand the PROX reaction kinetics. The microkinetic model was solved for a $H_2$ partial pressure of 1 bar. The CO partial pressure was set to be in the range of $5 \times 10^{-5}$ and 0.01 bars. A low CO pressure of $5 \times 10^{-5}$ bar was considered due to the need to reduce the CO concentration to ~50 ppm. The partial pressures of $O_2$, $H_2O$ and $CO_2$ were all set to be 0.01 bar. At 353K and a CO partial pressure of 0.01 bar, the turnover frequency (TOF) of $O_2$ consumption was calculated to be 33.46/s and the selectivity to $CO_2$ is ~100%. At a CO pressure of $5 \times 10^{-5}$ bar, the selectivity to $CO_2$ still reached ~100%. FIG. 27 shows a low apparent activation energy of 0.45 eV for the oxygen consumption. The reaction order of CO ($5 \times 10^{-5}$ to 0.01 bar) and $O_2$ (0.01-1 bar) were calculated to be 1 and 0 at 353 K, respectively. Even if the temperature deceased to 300 K, a high TOF of 2.38/s was obtained which is comparable to the one found for Pt-supported $Fe_1(OH)_x$ (2.1/s).

To better understand the high activity and selectivity of CO oxidation obtained from the microkinetic analysis, the free energy profiles were plotted with a CO partial pressure of 0.01 bar. Along Path-a(N) and b(N), the effective barriers of the first and second CO oxidation were calculated to be 0.74 and 0.77 eV, respectively, as compared with 1.20 and 1.56 eV for the oxidation of the first and the second $H_2$. If the dissociation of $H_2O$ is involved in the reaction, the effective barrier for the first CO oxidation along Path-c(N) is 0.78 eV, as compared to 1.47 eV for the $H_2$ along Path-d(N). The effective barrier of the second CO and $H_2$ oxidation along Path-c(N) and Path-d(N) are the same as in Path-a(N) and Path-b(N), respectively. Even if the CO partial pressure was reduced to $5 \times 10^{-5}$ bar, the effective barriers of CO oxidation were only ~0.94 eV, noticeably lower than those of the $H_2$ oxidation, hence the high selectivity to $CO_2$.

Example 6

Figure 28:
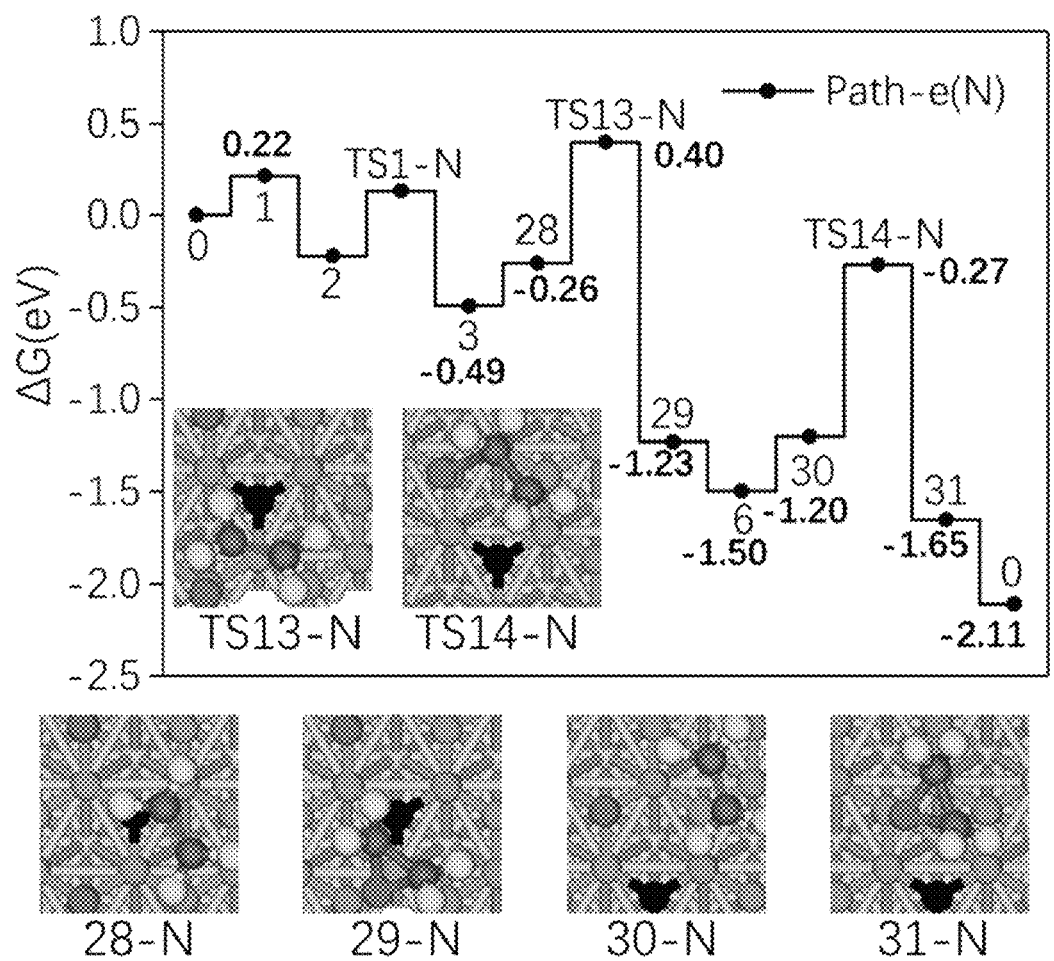
FIG. 28 presents free energy profiles of ethylene epoxidation on N-GR/Ni(111) at 423K.

The ethylene epoxidation reaction over N-GR/Ni(111) was investigated. The partial pressures of all gas phase molecules were set to be 1 bar. FIG. 28 presents the calculated energy profiles of ethylene epoxidation on N-GR/Ni(111). The physiosorbed ethylene on N-GR/Ni(111) reacts with oxygen through an Eley-Rideal mechanism after the facile dissociation of the chemisorbed $O_2$. Interestingly, since ethylene is not chemisorbed, an oxametallacycle intermediate of ethylene epoxidation typical for silver catalysts that processes both ethylene oxide and acetaldehyde is avoided. Ethylene can react with the first oxygen readily with an effective energy barrier of 0.89 eV, while the second ethylene epoxidation has a higher barrier of 1.23 eV. The relatively difficult epoxidation of the second ethylene is due to the stronger adsorption energy of the second oxygen (see Table 2, below).

A steady state microkinetic model was developed and solved for the epoxidation at 423K with ethylene, oxygen and ethylene oxide partial pressures of 10, 1 and 1 bar, respectively. The TOF of ethylene oxide formation was calculated to be 0.41/s. The appreciable TOF suggests that N-GR/Ni(111) can be a low temperature ethylene epoxidation catalyst.

To understand the high activity of ethylene epoxidation on N-GR/Ni(111), the adsorption energies of an oxygen atom and one hydrogen atom on a pre-adsorbed oxygen on several surfaces was computed. Table 1 shows that the adsorption behavior of O and H on N-GR/Ni(111) resemble that on Ag(111) while contrasts those on Pd(111), Pt(111) and Rh(111).

TABLE 2

|  | $E_{ads}(O)$/eV | $E_{ads}(H)$/eV |
| --- | --- | --- |
| 1$^{st}$ oxygen of N-GR/Ni(111) | −0.44 | −1.64 |
| 2nd oxygen of N-GR/Ni(111) | −0.87 | −1.25 |
| Ag(111) | −0.87 | −1.53 |
| Pd(111) | −1.72 | −0.56 |
| Pt(111) | −1.52 | −0.38 |
| Rh(111) | −2.41 | −0.31 |

While certain embodiments of the disclosed subject matter have been described using specific terms, such description is for illustrative purposes only, and it is to be understood that changes and variations may be made without departing from the spirit or scope of the subject matter.

The invention claimed is:

1. A method for oxidation of methane to form methanol comprising:
adsorbing oxygen on a catalyst, wherein the oxygen is chemisorbed on the catalyst, the catalyst comprising an atomic monolayer comprising graphene or hexagonal boron nitride, the catalyst further comprising a transition metal single atom dopant in a lattice of the atomic monolayer, wherein the atomic monolayer is covalently bonded to a surface of a support, the support comprising nickel (111) at the surface;
contacting the adsorbed oxygen with methane, upon which the methane is physisorbed on the catalyst and the methane is oxidized to form methanol.

2. The method of claim 1, wherein the method is carried out at a temperature of from about 350K to about 500K.

3. The method of claim 1, further comprising passing a fluid comprising the methane over the catalyst.

4. The method of claim 3, wherein the method comprises only a single pass of the fluid over the catalyst.

5. The method of claim 1, wherein the transition metal single atom dopant is scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), or mercury (Hg).

6. The method of claim 5, wherein the transition metal single atom dopant is Cu, Rh, Fe, Ir, or Mn.

7. The method of claim 5, wherein the transition metal single atom dopant is Cu or Rh.

8. The method of claim 1, wherein the atomic monolayer comprises graphene.

9. The method of claim 8, wherein the graphene comprises graphene featuring a MN4 motif.

10. The method of claim 1, wherein the atomic monolayer comprises hexagonal boron.

11. The method of claim 10, wherein the transition metal single atom dopant is inserted at a boron vacancy.

12. The method of claim 10, wherein the transition metal single atom dopant is inserted at a nitrogen vacancy.

13. The method of claim 1, wherein the support comprises greater than 50 atomic % of the nickel (III).

14. The method of claim 13, wherein the support comprises one or more additional metals.

15. The method of claim 1, wherein the support is in the form of a particulate.

16. The method of claim 15, wherein the support comprises greater than 50 atomic % of the nickel (III).

17. The method of claim 16, wherein the support comprises one or more additional metals.

* * * * *